US010752912B2

(12) United States Patent
Harig et al.

(10) Patent No.: US 10,752,912 B2
(45) Date of Patent: Aug. 25, 2020

(54) NUCLEIC ACID SEQUENCES AND PEPTIDES/PROTEINS OF THE FT FAMILY PROVIDING FLOWER REPRESSING PROPERTIES IN TOBACCO AND TRANSGENIC PLANTS TRANSFORMED THEREWITH

(71) Applicant: Fraunhofer-Gesellschaft zur Foerderung der angewandten Forschung e.V., Munich (DE)

(72) Inventors: Lena Harig, Muenster (DE); Dirk Pruefer, Muenster (DE); Rainer Fischer, Aachen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1224 days.

(21) Appl. No.: 14/390,148

(22) PCT Filed: Mar. 28, 2013

(86) PCT No.: PCT/EP2013/056727
§ 371 (c)(1),
(2) Date: Oct. 2, 2014

(87) PCT Pub. No.: WO2013/149941
PCT Pub. Date: Oct. 10, 2013

(65) Prior Publication Data

US 2015/0353945 A1 Dec. 10, 2015

(30) Foreign Application Priority Data

Apr. 4, 2012 (EP) .................................... 12163187

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/827* (2013.01); *C12N 15/8274* (2013.01)

(58) Field of Classification Search
None
See application file for complete search history.

(56) References Cited

U.S. PATENT DOCUMENTS 7,470,831 B1 12/2008 Chu et al.
2003/0093835 A1* 5/2003 Weigel ................ C07K 14/415 800/287
2004/0126843 A1 7/2004 Demmer et al.
2005/0108791 A1 5/2005 Edgerton
2008/0047029 A1 2/2008 Kardailsky et al.
2009/0183270 A1* 7/2009 Adams ............... C07K 14/4702 800/260
2010/0275330 A1 10/2010 Spangenberg et al.
2012/0167247 A1 6/2012 Kraus et al.

FOREIGN PATENT DOCUMENTS

JP 2007202441 A 8/2007
WO WO9953070 A1 10/1999
WO 2000050615 8/2000
WO 2010025888 A2 3/2010
WO 2010039750 A3 4/2010

OTHER PUBLICATIONS

Carmel-Goren et al. Plant molecular biology 52.6 (2003): 1215-1222.*
Ho et al. (The Plant Cell (2014): tpc-113). (Year: 2014).*
Guo et al (2004, Proc. Natl. Acad. Sci. USA 101: 9205-9210). (Year: 2004).*
Jones et al. (American Journal of Botany 94(6):935-947, 2007). (Year: 2007).*
GenBank Accession XP 015074903, dated Dec. 23, 2015. (Year: 2015).*
GenBank Accession NM 001321052 (2003). (Year: 2003).*
GenBank Accession XM 016595294 (2012). (Year: 2012).*
GenBank Accession AAO31793 dated Jan. 22, 2004. (Year: 2004).*
GenBank Accession MG733984 dated Feb. 21, 2018. (Year: 2018).*
Ahn et al. (The EMBO Journal (2006) 25, 605-61). (Year: 2006).*
Database EMBL (Online), Dec. 11, 2005, "KL4B.103B04F.051103T7 KL4B Nicotiana tabacum cDNA clone KL4B.103B04, mRNA sequence", XP002698090.
Ji Hoon Ahn et al, "A divergent external loop confers antagonistic activity on floral regulators FT and TFL1", The EMBO Journal, vol. 25, No. 3, Feb. 8, 2006.
P.A. Pin et al., "An Antagonistic Pair of FT Homologs Mediates the Control of Flowering Time in Sugar Beet", Science, vol. 330, No. 6009, Dec. 3, 2010.
Lena Harig et al., "Proteins from the Flowering Locus T-like subclade of the PEBP family act antagonistically to regulate floral initiation in tobacco", Plant Journal, vol. 72, No. 6, Dec. 2012.
Goren et al., "The Self-Pruning Gene Family in Tomato," Plant Molecular Biology, vol. 52, p. 1215-1222 (2003).

(Continued)

*Primary Examiner* — Charles Logsdon
(74) *Attorney, Agent, or Firm* — Duane Morris LLP

(57) ABSTRACT

The present invention is directed to nucleic acid sequences coding for a protein which, (1) under a respective promoter, is able to suppress or repress or delay flowering of a plant, and (2) includes the motive "NAPDIIDS" (SEQ ID NO: 10) or, in preferred cases, "VNAPDIIDS" SEQ ID NO: 67), with the exception of the nucleic acid of the gene StSP5G or a part thereof. Preferably, the nucleic acid sequence belongs phylogenetically to the FT-clade of the PEBP gene family, wherein the motive "(V)NAPDIIDS" (SEQ ID NO: 68) is in place of the "(V)YAPGW" motive (SEQ ID NO: 69) of the flowering promoting proteins AtFT and BvFT2.

The invention is further directed to peptides or proteins, obtainable by expression of the nucleic acid of any of the preceding claims, vectors, comprising a nucleic acid sequence as defined above, and to plants, parts of plants, or seed of plants, the plants comprising such a nucleic acid sequence.

15 Claims, 14 Drawing Sheets

Specification includes a Sequence Listing.

(56) References Cited

OTHER PUBLICATIONS

KL4B.103B04F.051103T7 KL4B Nicotiana tabacum cDNA clone KL4B.103B04, mRNA sequence. GenBank: DV999455.1, Dec. 9, 2005.
Database Geneseq [Online] Feb. 22, 2007 (Feb. 22, 2007), "*Arabidopsis thaliana* stress tolerance protein—SEQ ID 23210", retrieved from EBI accession No. GSP:AEN37923.
Database Geneseq [Online] Feb. 22, 2007 (Feb. 22, 2007), "*Arabidopsis thaliana* stress tolerance protein—SEQ ID 23211.", retrieved from EBI accession No. GSP:AEN37924.
Database Geneseq [Online] Feb. 22, 2007 (Feb. 22, 2007), "*Arabidopsis thaliana* stress tolerance protein—SEQ ID 23212.", retrieved from EBI accession No. GSP:AEN37925.
Yoshie Hanzawa et al.; A Single Amino Acid Converts a Repressor to an Activator of Flowering, Cell and Development Biology, Proc. Natl. Acad. Sci. U.S.A, vol. 102, 7748-7753, May 24, 2005.
GenBank Accession AY186736, "Lycopersicon esculenturn SP5G (SP5G) gene, complete cds", dated Jan. 22, 2004.
GenBank Accession ADM92610, "flowering locus T-like protein FT2 [*Beta vulgaris*]", dated Dec. 6, 2010.
Office Action in Korean Application No. 10-2014-7031014, dated Oct. 18, 2018, with English translation.

* cited by examiner

<210> SEQ ID NO: 1
<211> Length: 534
<212> Type: DNA
<213> Organism: Nicotiana tabacum
<400> Sequence Nt*FT1*

```
atgtcaagac tagatccttt aatagtatct ggggtaatag gagatgtttt ggattcattt  60
acaaggtcta tagactttag tgtggtttat aataataggg tacaagtcta caatggttgt 120
ggtttgaggc cttcacaaat tgtcaaccaa cctagggttg acattggagg agatgatctt 180
cgcacttttt acactatggt tatggtggat ccagatgctc caaccccaag caacccaaac 240
ctgagggagt atctgcactg gctggtcaca gatatcccag caaccacagg agcaaacttt 300
ggcaatgaaa ttatacgata cgagagtcca cgaccttcac tgggaattca tcgctatatt 360
ttcgtgttgt ttcagcaatt ggatcgagag gttgtgaatg ctcctgatat aattgattct 420
cgtcagaatt ttaacacaag agactttgcg agatttcata atctcaattc gcctgttgct 480
gctgtttact tcaattgcaa tagagaaggt ggtaccggtg gccgtcacct ataa       534
```

Figure 1

<210> SEQ ID NO: 2
<211> Length: 534
<212> Type: DNA
<213> Organism: Nicotiana tabacum
<400> Sequence Nt*FT2*

```
atgttaagag caaatccttt agtagtatct ggtgtaatag gagatgtatt ggatccattt  60
acaaagtctg tagactttga tgtggtttac aataataatg tgcaggtcta caatggctgt 120
ggattgaggc cttcacaaat tgtcaaccaa cctagggttg acattgcagg agatgatttt 180
cgcacttttt acactctggt tatggtggat ccagatgctc caaccccgag caacccaaat 240
ctgagggagt atctccattg gctggtcaca gatatccctg caaccacaga agcaaccttt 300
ggcaatgaaa ttgtaagtta tgagagacca caaccttcat tgggaattca tcgctatatt 360
ttcgtgttgt ttcggcaatt ggatcgagag gttgtgaatg ctcctgatat aattgattct 420
cgtgagattt ttaacactag agactttgca aggtttcacg gtctcaattt gcctgttgcc 480
gctgtttact tcaattgcaa tagggaaggc ggtaccggtg gccgtcacct ataa       534
```

Figure 2

<210> SEQ ID NO: 3
<211> Length: 534
<212> Type: DNA
<213> Organism: Nicotiana tabacum
<400> Sequence Nt*FT3*

```
atgtcaagac tagatccttt aatagtatct ggtgttatag gagatgtatt ggatccattt 60
acaaggtcta tagactttaa tgttgtttac aataatagga tgcaagtcta caatggctgt 120
ggtttgaggc cttcacaaat tgtccaccaa cctagggttg acgtgggagg agatgatctt 180
cgcacttttt acactctggt tatggtggat ccagatgctc caaccccgag caatccaaac 240
cagagggagt atctccactg gctggtcaca aatatcccag caaccacagg agcacacttc 300
gggaatgaaa ttatacaata cgagagtcca cgaccttcat tgggaattca tcgctatatt 360
tttgtgctgt ttcgacaatt gactcgagat gttgtgaatg ctcctgatat aattgattct 420
cgtgagaatt ttaacacaag agactttgca aggttttacg atctcaattc gcctgttgct 480
gctatgtact tcaatagcaa tagggaaagt ggtactggtg gccgtcacct ataa       534
```

Figure 3

<210> SEQ ID NO: 4
<211> Length: 525
<212> Type: DNA
<213> Organism: Nicotiana tabacum
<400> Sequence Nt*FT4*

```
atgccaagaa tagatccttt gatagttggt cgtgtggtag gagatgtttt agatccattc  60
acaaggtctg ttgatcttag agtggtttac aataataggg aagtcaacaa tgcatgtggc 120
ttgaaacctt ctcaaattgt tacgcaacct agggttcaaa ttggagggga tgatcttcgc 180
aacttttaca ctctggttat ggtggatcct gatgctccaa gcccaagcaa ccctaacctg 240
agggagtatc tacactggct ggtcacagat atcccagcaa ctacagatac aagctttgga 300
aatgaagtta tatgctacga gaatccacaa ccatcattgg gaattcatcg ctttgttttc 360
gtgttgtttc gacaattggg tcgcgaaact gtgtatgcac caggttggcg tcagaatttc 420
agcacaagag actttgcaga agtttacaat cttggtttgc ccgtttctgc tgtttacttc 480
aattgccata gggagagtgg tactggtggc cgccgcgcat attaa                 525
```

Figure 4

```
<210> SEQ ID NO: 5
<211> Length: 177
<212> Type: PRT
<213> Organism: Nicotiana tabacum
<400> Sequence NtFT1
Met Ser Arg Leu Asp Pro Leu Ile Val Ser Gly Val Ile Gly Asp Val
1               5                   10                  15
Leu Asp Ser Phe Thr Arg Ser Ile Asp Phe Ser Val Val Tyr Asn Asn
            20                  25                  30
Arg Val Gln Val Tyr Asn Gly Cys Gly Leu Arg Pro Ser Gln Ile Val
        35                  40                  45
Asn Gln Pro Arg Val Asp Ile Gly Gly Asp Asp Leu Arg Thr Phe Tyr
    50                  55                  60
Thr Met Val Met Val Asp Pro Asp Ala Pro Thr Pro Ser Asn Pro Asn
65                  70                  75                  80
Leu Arg Glu Tyr Leu His Trp Leu Val Thr Asp Ile Pro Ala Thr Thr
                85                  90                  95
Gly Ala Asn Phe Gly Asn Glu Ile Ile Arg Tyr Glu Ser Pro Arg Pro
            100                 105                 110
Ser Leu Gly Ile His Arg Tyr Ile Phe Val Leu Phe Gln Gln Leu Asp
        115                 120                 125
Arg Glu Val Val Asn Ala Pro Asp Ile Ile Asp Ser Arg Gln Asn Phe
    130                 135                 140
Asn Thr Arg Asp Phe Ala Arg Phe His Asn Leu Asn Ser Pro Val Ala
145                 150                 155                 160
Ala Val Tyr Phe Asn Cys Asn Arg Glu Gly Gly Thr Gly Gly Arg His
                165                 170                 175
Leu
177
```

Figure 5

```
<210> SEQ ID NO: 6
<211> Length: 177
<212> Type: PRT
<213> Organism: Nicotiana tabacum
<400> Sequence NtFT2
Met Leu Arg Ala Asn Pro Leu Val Val Ser Gly Val Ile Gly Asp Val
1               5                   10                  15
Leu Asp Pro Phe Thr Lys Ser Val Asp Phe Asp Val Val Tyr Asn Asn
            20                  25                  30
Asn Val Gln Val Tyr Asn Gly Cys Gly Leu Arg Pro Ser Gln Ile Val
        35                  40                  45
Asn Gln Pro Arg Val Asp Ile Ala Gly Asp Asp Phe Arg Thr Phe Tyr
    50                  55                  60
Thr Leu Val Met Val Asp Pro Asp Ala Pro Thr Pro Ser Asn Pro Asn
65                  70                  75                  80
Leu Arg Glu Tyr Leu His Trp Leu Val Thr Asp Ile Pro Ala Thr Thr
                85                  90                  95
Glu Ala Thr Phe Gly Asn Glu Ile Val Ser Tyr Glu Arg Pro Gln Pro
            100                 105                 110
Ser Leu Gly Ile His Arg Tyr Ile Phe Val Leu Phe Arg Gln Leu Asp
        115                 120                 125
Arg Glu Val Val Asn Ala Pro Asp Ile Ile Asp Ser Arg Glu Ile Phe
    130                 135                 140
Asn Thr Arg Asp Phe Ala Arg Phe His Gly Leu Asn Leu Pro Val Ala
145                 150                 155                 160
Ala Val Tyr Phe Asn Cys Asn Arg Glu Gly Gly Thr Gly Gly Arg His
                165                 170                 175
Leu
177
```

Figure 6

<210> SEQ ID NO: 7
<211> Length: 177
<212> Type: PRT
<213> Organism: Nicotiana tabacum
<400> Sequence NtFT3

```
Met Ser Arg Leu Asp Pro Leu Ile Val Ser Gly Val Ile Gly Asp Val
1               5                   10                  15
Leu Asp Pro Phe Thr Arg Ser Ile Asp Phe Asn Val Val Tyr Asn Asn
            20                  25                  30
Arg Met Gln Val Tyr Asn Gly Cys Gly Leu Arg Pro Ser Gln Ile Val
        35                   40                 45
His Gln Pro Arg Val Asp Val Gly Gly Asp Asp Leu Arg Thr Phe Tyr
    50                  55                  60
Thr Leu Val Met Val Asp Pro Asp Ala Pro Thr Pro Ser Asn Pro Asn
65                  70                  75                  80
Gln Arg Glu Tyr Leu His Trp Leu Val Thr Asn Ile Pro Ala Thr Thr
                85                  90                  95
Gly Ala His Phe Gly Asn Glu Ile Ile Gln Tyr Glu Ser Pro Arg Pro
            100                 105                 110
Ser Leu Gly Ile His Arg Tyr Ile Phe Val Leu Phe Arg Gln Leu Thr
        115                 120                 125
Arg Asp Val Val Asn Ala Pro Asp Ile Ile Asp Ser Arg Glu Asn Phe
    130                 135                 140
Asn Thr Arg Asp Phe Ala Arg Phe Tyr Asp Leu Asn Ser Pro Val Ala
145                 150                 155                 160
Ala Met Tyr Phe Asn Ser Asn Arg Glu Ser Gly Thr Gly Gly Arg His
                165                 170                 175
Leu
177
```

Figure 7

```
<210> SEQ ID NO: 8
<211> Length: 174
<212> Type: PRT
<213> Organism: Nicotiana tabacum
<400> Sequence NtFT4
Met Pro Arg Ile Asp Pro Leu Ile Val Gly Gly Val Val Gly Asp Val
1               5                   10                  15
Leu Asp Leu Phe Thr Arg Ser Val Asp Leu Arg Val Val Tyr Asn Asn
            20                  25                  30
Lys Glu Val Asn Asn Ala Cys Gly Leu Lys Pro Ser Gln Ile Val Thr
        35                  40                  45
Gln Pro Arg Val Gln Ile Gly Gly Asp Asp Leu Arg Asn Phe Tyr Thr
    50                  55                  60
Leu Val Met Val Asp Pro Asp Ala Pro Ser Pro Ser Asn Pro Asn Leu
65                  70                  75                  80
Arg Glu Tyr Leu His Trp Leu Val Thr Asp Ile Pro Ala Thr Thr Asp
                85                  90                  95
Thr Ser Phe Gly Asn Glu Val Val Cys Tyr Glu Ser Pro Gln Pro Ser
            100                 105                 110
Met Gly Ile His Arg Phe Val Phe Ala Leu Phe Arg Gln Leu Gly Arg
        115                 120                 125
Glu Thr Val Tyr Ala Pro Gly Trp Arg Gln Asn Phe Asn Thr Arg Asp
    130                 135                 140
Phe Ala Glu Leu Tyr Asn Leu Gly Leu Pro Val Ala Ala Val Tyr Phe
145                 150                 155                 160
Asn Cys His Arg Glu Ser Gly Thr Gly Gly Arg Arg Ala Tyr
                165                 170                 174
```

Figure 8

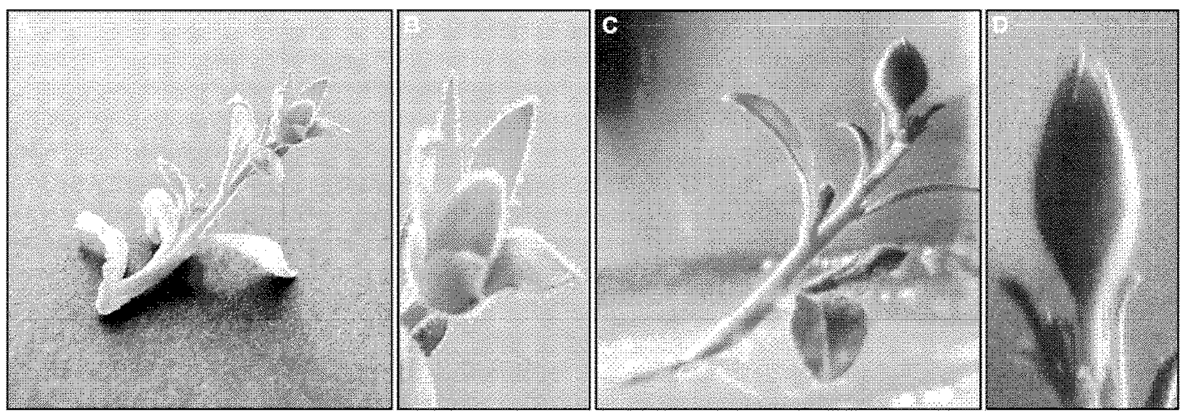

Figure 11

```
AtFT          SI----NIRISRPNRSITKTGQR-ETLDR  45
AtTFL1        ENM-GTRVIIGRFTPTTKNSNK-KQSHEF  48
NtFT1         SR------LISGSTRSIDSVNNRVQYCGR  44
NtFT2         LR------AVSGPTKSVDDVNNNVQYCGR  44
NtFT3         SR------LISGPTRSIDNVNNRMQYCGR  44
NtFT4         PR------IIGGLTRSVDRVNNK-ENACGK  43
CET1          A----SRVVVARSNPSVKNINGSKQFHEM  46
CET2          G----SKMSVGRYTPSVKSTNSSKHYHEF  46
CET4          G----SKMSVGRYTPSVKSTNSSKHYHEF  46
StSP5G        PR-------ISGPTRCVDGVNNR-VYCAR  42
SlSP5G        PR-------ISGPTRCVDGVNNR-VYCSR  42
BvFT1         PRTSASAPRVGGPERSVTKSNNR-NNGDR  49
BvFT2         PR----APRVGRPSRTVNRSSNR-DNCER  45
              *         :.* :. *:*:*:: *     : : :.    * *.  : *
                                                          ★
AtFT          QQNGENFVVSHLA  95
AtTFL1        SSSHGSFIVGFLG  98
NtFT1         QVNGDTFVATNLA  94
NtFT2         QVNADTFVATNLA  94
NtFT3         QVHGDTFVATNQA  94
NtFT4         QVTGDNFVASNLA  93
CET1          VAAGESATVGYLG  96
CET2          STSHGSFIVGYLG  96
CET4          STSHGSFIVGYLG  96
StSP5G        QVNGDIFVANNLA  92
SlSP5G        QVNDDTFVANNLA  92
BvFT1         QVNGDTCVASHQG  99
BvFT2         QVNGDTFVASHLG  95
              : :  :* *:: * :::  :*::* ***.* **:*  :*:***:**:**.
                                                                 ★
AtFT          GTTNCNSTAVILGQTY-APG---WN 141
AtTFL1        DATKSLRSIFVKQRVFPNIP---SH 145
NtFT1         GANNRSRSLYVLDEVN-APDIIDSN 143
NtFT2         EATNSRQSLYVLDEVN-APDIIDSI 143
NtFT3         GAHNQSRSLYVLTDVN-APDIIDSN 143
NtFT4         DTSNCSQSMFALGETY-APG---WN 139
CET1          DSSRSSKVIYLSGQTK-PAA---TH 142
CET2          DCSKGMRNIFLKKQTLTAPL---SR 143
CET4          DCSRGMRNIFLKKQTLSAPL---SR 143
StSP5G        GATNHSRSMYVLGEAN-APDIIDSN 141
SlSP5G        GATNGSRSMYVLGCDAD-APDIIDSN 141
BvFT1         SASEYNRSTFALGQTN-APQ---QN 145
BvFT2         GASQCNRSVFVLGQTY-APG---WN 141
              :*   **.*:: ** * *  **** :: *::*     :        *:

AtFT          EEIYNGLVCSGCGG-L 175          (SEQ ID NO: 70)
AtTFL1        KVEYDGLVA--TAA-R 177          (SEQ ID NO: 71)
NtFT1         DRFHNNSVCGGTGG-L 177          (SEQ ID NO: 72)
NtFT2         DRFHGNLVCGGTGG-L 177          (SEQ ID NO: 73)
NtFT3         DRFYDNSMSSGTGG-L 177          (SEQ ID NO: 74)
NtFT4         DELYNGLVCSGTGGAY 174          (SEQ ID NO: 75)
CET1          RAENGGSVA--TAA-R 174          (SEQ ID NO: 76)
CET2          KEENEGSVC--TAA-R 175          (SEQ ID NO: 77)
CET4          KEENEGSAC--TAA-R 175          (SEQ ID NO: 78)
StSP5G        DRFHNGLVCGGTGD-L 175          (SEQ ID NO: 79)
SlSP5G        DRFHNGLVCGGTGG-L 175          (SEQ ID NO: 80)
BvFT1         DELYNGLVCGGCGG-F 179          (SEQ ID NO: 81)
BvFT2         DELYNGLVCGGSGG-L 175          (SEQ ID NO: 82)
              *:** ::    :. **** ::*.:**   . *:
```

Figure 10

| | leaf number | height in cm | stem diameter in cm | biggest leaf size in cm |
|---|---|---|---|---|
| WT | 15 - 19 | 81 | 1,2 | 43 x 21 |
| 35S:Nt *FT2* | 114 - 119 | 297 - 355 | 4,5 | 65 x 22 |
| 35S:Nt *FT3* | 118 | 290 | 3,9 | 59 x 21 |

segment B

| | | |
|---|---|---|
| NtFT1 | LDREVV**N**-AP**DIIDS**RQN | (SEQ ID NO: 15) |
| NtFT4 | LGRETV**Y**-AP**G**---**W**RQN | (SEQ ID NO: 18) |
| $NtFT1_{swap}$ | LDREVV**Y**-AP**G---W**RQN | (SEQ ID NO: 83) |

NUCLEIC ACID SEQUENCES AND PEPTIDES/PROTEINS OF THE FT FAMILY PROVIDING FLOWER REPRESSING PROPERTIES IN TOBACCO AND TRANSGENIC PLANTS TRANSFORMED THEREWITH

SEQUENCE LISTING

The instant application contains a Sequence Listing which has been submitted electronically in ASCII format and is hereby incorporated by reference in its entirety. Said ASCII copy, created on Aug. 24, 2015, is named F6245-00038_SL.txt and is 44,132 bytes in size.

The present invention relates to novel nucleic acid sequences, amino acid, peptide and protein sequences derived thereof, and plants and their progeny transformed therewith. The nucleic acid sequences confer a delay or inhibition of flowering. Further, the invention relates to methods for engineering non-flowering plants in order to ensure containment of transgenic plants, especially for such, that can propagate vegetatively.

The transition from vegetative to reproductive growth is an important feature of the life cycle of plants. Accurate timing of the initiation of flowering is essential for plants to ensure the reproductive success. In agriculture and forestry, this transition is also very important because it significantly influences yield and biomass. As an example, the development of flowers is an obstacle in respect to the aim of producing a high amount of biomass, since development of the flowers in plants is often accompanied by termination of the vegetative growth and senescence. Therefore, a modulation of the time of flowering, specifically a delay thereof, should result in an increase of biomass because the plant is enabled to convert its full energy into vegetative growth and senescence of the plant material is inhibited or at least deferred.

An interlaced network of signaling pathways involving exogenous signals like photoperiod and vernalization tightly controls the developmental step of flowering in the plant lifecycle by regulating the expression of a large number of genes. During evolution, duplication of key genes controlling flowering appeared to play an important role in view of the fact that novel functions were established by homolog genes. Prominent examples are members of the plant phosphatidyl ethanolamine-binding protein (PEBP) family, a family also found in bacteria and animals, where they are involved in various biological processes, being for example protease and kinase inhibitors. In plants, however, members of the PEBP family play an important role in shoot meristem identity and act in the control of flowering time. The most prominent member is FLOWERING LOCUS T (FT). FT senses floral inductive conditions in the leaves and triggers floral development in the shoot apical meristem (SAM), being therefore the mobile floral signal molecule, described as the "florigene", a term already defined in 1937 by Chailakhyan. Studies of homologs in several species revealed that FT has a species spanning universal role in promoting flowering, such as in dicotyledonous species like *Arabidopsis*, tomato, poplar, apple, cucurbits, sugar beet (Pin et al., 2010), and many others.

In the model plant *Arabidopsis thaliana*, FT expression is activated in the phloem companion cells of the leaves by the B-box zinc finger transcription factor CONSTANS (CO) under inductive long-day conditions (LD) due to the fact that the CO protein is only stabilized in the light. Subsequently, FT protein enters the sieve elements of the sieve tubes and is transported via the mass flow to the SAM, where it interacts with the bZIP transcription factor FD; both together activate the downstream targets of floral development such as the second floral integrator SUPPRESSOR OF OVER-EXPRESSION OF CONSTANS 1 (SOC1) and the floral meristem identity gene *APETALA*1 (API). The closest homolog to FT in *Arabidopsis* is TWIN SISTER OF FT (TSF), which evolved by gene duplication. TSF is a direct regulatory target of CO and acts as a floral promoter, thus operating redundantly to FT. Under non-inductive short day conditions (SD) flowering of the facultative LD plant *Arabidopsis* is controlled via the FT-independent gibberellin pathway, which directly activates the expression of SOC1.

Another important key regulator of flowering in *Arabidopsis* is TERMINAL FLOWER 1 (TFL1); its homolog CENTRORADIALES from *Antirrhinum majus* is the founding member of the plant PEBP gene family. Although sharing high sequence similarity with FT, TFL1 is a floral repressor and responsible for inflorescence architecture, thus being functionally antagonistic to its relative FT. However, the substitution of a few defined amino acids can convert TFL1 into a flowering inducer and FT into a flowering repressor, respectively (Hanzawa Y., Money T., and Bradley D. (2005). A single amino acid converts a repressor to an activator of flowering. Proc. Natl. Acad. Sci. U.S.A 102, 7748; Ahn J. H., Miller D., Winter V. J., Banfield M. J., Lee J. H., Yoo S. Y., Henz S. R., Brady R. L., and Weigel D. (2006). A divergent external loop confers antagonistic activity on floral regulators FT and TFL1. EMBO J. 25, 605-614). A specific delimitation of FT and TFL is performed on the transcriptional level. FT is merely expressed in the leaves and subsequently transported to the SAM, while the expression and translation of TFL1 takes only place in the SAM. Both proteins, TFL and FT were reported to interact with the same co-factor FD in the shoot apex, that way regulating transcriptional repression or activation of target genes: The TFL/FD complex represses the transcription of floral meristem identity genes, which are activated by the FT/FD complex. Thus, one has to assume a general co-ordination of two PEBP proteins in the regulation of flower development which have antagonistic functions and each represent a sub family of the PEBP family. Homologs of TFL1 with similar function in repressing flowering are widespread in other species and constitute one of the three main clades of the PEBP family. Beside FT, TSF and TFL, three more PEBP family members have been characterized in *Arabidopsis*, namely MOTHER OF FT AND TFL1 (MFT), which seems to act redundantly to FT and BROTHER OF FT AND TFL1 (BFT) as well as *ARABIDOPSIS THALIANA* CENTRORADIALES (ATC), which show redundant activity to TFL1.

Although FT and TFL 1 are regarded as belonging to the same family and have 57% identity in their amino acid sequence, they function as antagonists in the development of flowering and, moreover, each represent a phylogenetically different subfamily of the PEBP family.

The prior art suggests a modulation of the time of flowering. This can be achieved by overexpression of repressors of flower development, or the expression of activators of flower development is down regulated via RNA interference (RNAi). However, in all these cases, flowering of the plant is only delayed, but never inhibited. One example is the protein FLC of *Arabidopsis*, which can be used as a repressor of flower development, in order to defer the time of flowering, see WO 2000/050615.

Recently, in sugar beet an alternative way in repressing flowering was identified. In this plant species, an antagonistic pair of FT homologs (BvFT1 and BvFT2) evolved, regulating floral transition, where BvFT1—although being an FT homolog—represses flowering while BvFT2 promotes it (Pin et al., Science 330, 1397 (2010)). It has been suggested to modulate the expression of the genes of these proteins, specifically by downregulation or suppression of the BvFT2 gene or upregulation of the BvFT1 gene, in order to obtain a delay of the vernalization response in growing sugar beet plants or to cause the sugar beet plants to develop a non-bolting phenotype, see WO 2010/025888. However, since bolting resistant sugar beet would not flower, due to the lack of bolting, no seeds would be produced. In order to be able to maintain, multiply and commercialize bolting resistant sugar beet plants, the said modulation needs to be conditional or latent, because sugar beet cannot be multiplied vegetatively. Consequently, it is suggested to use inducible promotors as hybrid constructs for transfection. In the examples, BvFT2 was silenced by deriving a RNAi cassette therefrom. The flowering delay observed was between zero and—in one of 29 cases—over 87 days. Moreover, BvFT1 was expressed under the control of the constitutive Ubi3 promoter from *Arabidopsis* both in annual and biennial transgenic plants. These showed a delay in bolting ranging from few weeks to more than three months.

Since flowering time has an enormous impact on biomass production it is necessary to understand how flowering time is regulated in species of agronomical interest. Although tobacco (*Nicotiana tabacum*), like many other members of the Solanaceae plant family, is of major economic importance as a crop, relatively little is known about floral regulation in tobacco and only few genes are analyzed. For in-depth research on flower development, tobacco is of great interest since this species is most likely the result of a tetraploidization event and harbors the genome of the LD cultivar *Nicotiana sylvestris* combined with that of a close relative of the facultative SD cultivar *Nicotiana tomentosiformis*. However, in contrast to the model plant *Arabidopsis*, the molecular basis of flower development in tobacco is only poorly understood because only a few genes have been identified and characterized until now.

Transgenic plants expressing an inhibitor of flowering which is under the control of a conditional or latent promoter will former or later develop flowers—either undesired, or for obtaining progeny. Thus, sooner or later such plants will necessarily be the source for the production of pollen grains. It is evident that control of such pollen is difficult, in case the plants belong to commercially interesting crops, grown outside from greenhouses. Therefore, outcrossing with wild relatives and with corresponding crop plants is still possible and spreading of transgenes into nature cannot be circumvented.

It is an object or a problem of the present invention to overcome at least partly this disadvantage and provide a nucleic acid coding for an amino acid sequence capable of suppressing or delaying the development of blossoms or flowers, which preferably belongs to the FT clade by most of its amino acids and motive, but which in any case exhibits a partial sequence which deviates from all sequences and motive of FT proteins known in the art, imparting new and unique features to the plants transformed with constructs including said nucleic acid. In particular, said nucleic acid can be used for the generation of transgenic plants, preferably crops, which are either delayed in flowering or, even more preferred, are non-flowering and remain non-flowering over more than one vegetation period. The invention focuses thereby on the usage of plants, which can be multiplied vegetatively, e.g. tobacco or potato.

BRIEF DESCRIPTION OF THE DRAWINGS

FIG. 1-FIG. 8 show SEQ ID NO 1-SEQ ID NO 8, respectively.

In FIG. 9A, an alignment of the genomic and cDNA sequences reveals the exon-intron structure of Nt FT1-4, while FIG. 9B illustrates the assignment of the tobacco FT-homologs to the three PEBP family clades.

FIG. 10 shows a protein alignment of exemplarily chosen members of the plant PEBP family.

FIGS. 11A and 11B show shoots of plants wherein the coding region of Nt FT4 was cloned downstream of the constitutive promoter of the cauliflower mosaic virus (35S) and introduced into tobacco by Agrobacterium-mediated transformation. The phenotype was nearly identical to that caused by the overexpression of the Arabidopsis FT (35S:At FT), which served as a control in this experiment (FIGS. 11C and D).

FIG. 13K depicts a comparison of leaf number, height, stem diameter and leaf size between a flowering WT plant and the severe overexpressing tobacco lines 28 wat, while FIG. 13L depicts a comparison of apical (top), medial (middle) and basal (bottom) leaves between 28-week-old 35S:Nt $FT2_{L2}$, 35S:Nt $FT3_{L1}$ and a flowering, 8-week-old WT plant.

As shown in FIGS. 16A to 16C, transgenic Arabidopsis plants with a high expression level of 35S:Nt FT2 exhibit a late flowering phenotype accompanied with an increase in biomass under inductive LD conditions.

In FIGS. 18A and 18B, plants with a high expression level of either 35S:Nt FT1, 35S:Nt FT2 or 35S:Nt FT3 exhibit a late flowering phenotype under LD conditions.

Figure 9:
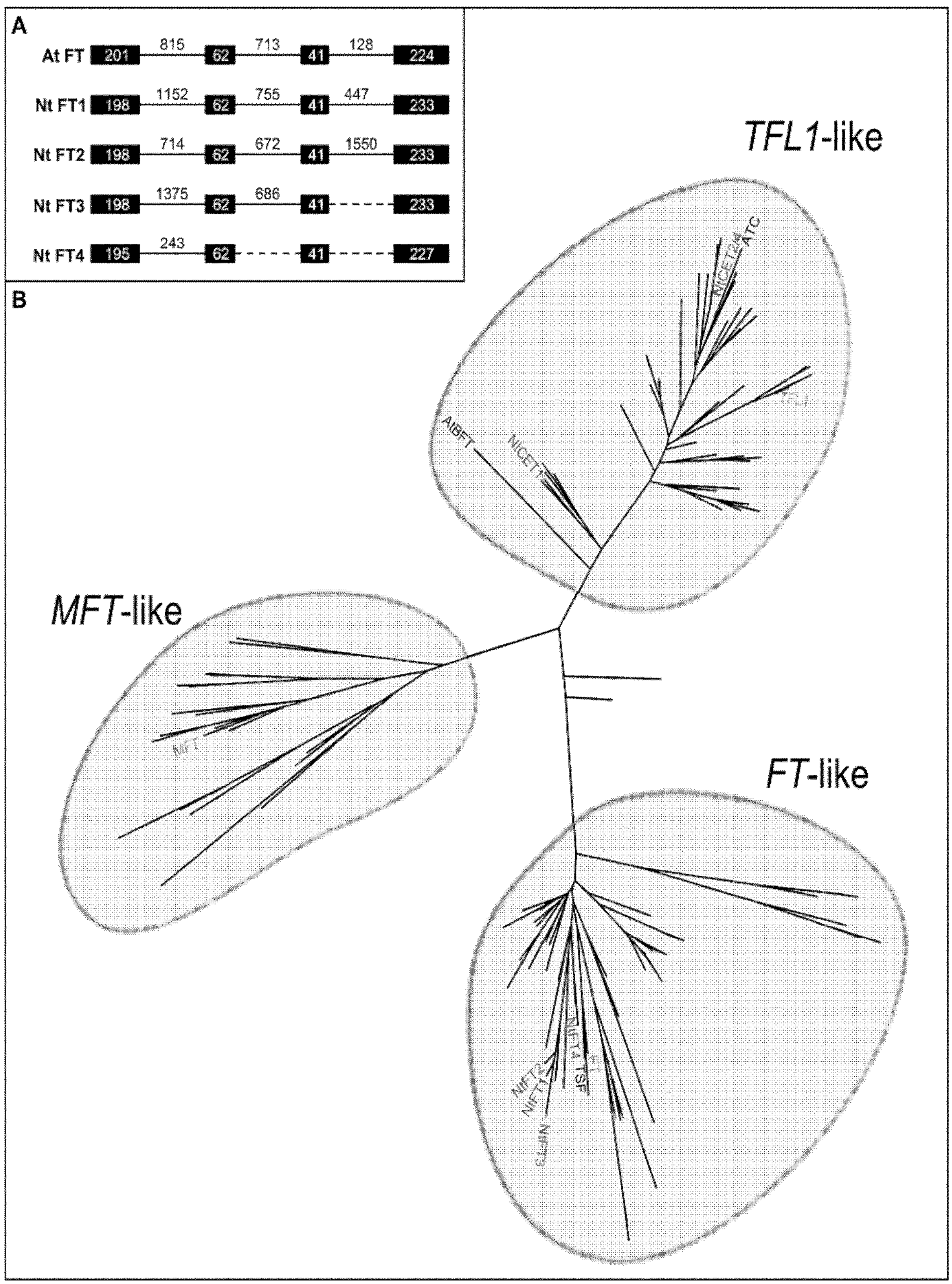

The inventors of the present invention were able to identify four FT homologs in tobacco, designated as Nt FT1-4 which phylogenetically belong to the FT subfamily, but have antagonistic functions in flower development. The function of these proteins was examined by overexpression. Surprisingly, it could be shown that plants overexpressing Nt FTs exhibit complete different phenotypes, ranging from very early flowering shoots in tissue culture (Nt FT4) to nonflowering, 9 month old and more than 5 m high giants (Nt FT1-3). Usually, a tobacco plant of the variety SR1 flowers around 6 to 8 weeks after germination and will reach a height of about 1 to 1.5 m at that time. By overexpression of one of the FTs which cause a repression of flowering, tobacco plants could be generated which grew purely vegetatively for at least nine months, and during said period reached a height of more than 5 m. The inventors have shown that this effect can be transferred to other species than tobacco, at least within the solanacea family. These results make it possible to use the said NtFT1, NtFT2 and NtFT3 or parts thereof for constructs which can be used to transform not only tobacco, but also other solanaceous plant species like potato. Moreover, plants of other plant families may be transformed, like those of the Brassicaceae or Asteraceae plant family, e.g. the rubber crop *Taraxacum koksaghyz*, (an Asteraceae) in order to repress floral transition. The chosen plant species should preferably be multiplied vegetatively.

FIG. 10 shows a protein alignment of exemplarily chosen members of the plant PEBP family. Columns of complete identical amino acids in all sequences in the alignment are designated with *; conserved substitutions are designated with :; semiconserved substitutes are designated with .. Asterisks mark amino acids essential for At FT vs. At TFL1 function (Ahn et al., 2006, see above) letters in italic mark amino acids mediating By FT1 vs. By FT2 function (Pin et al., 2010, see above). There is one non-conserved region where AtFT, NtFT4, as well as the flower-promoting protein from sugar beet, BvFT2, show the identical "YAPGW" motive (SEQ ID NO: 9).

The present invention provides a new class of proteins and nucleic acids coding for said proteins wherein the proteins (1) have repressing properties, and (2) include the motive "NAPDIIDS" (SEQ ID NO: 10) in place of the "YAPGW" motive (SEQ ID NO: 9) of all flowering promoting proteins. Furthermore, this motive also differs from the already characterized "NAPQQ" motive (SEQ ID NO: 11) of the flower repressing BvFT1 in the identical protein region. Preferably, (3) the proteins belong to the FT clade. The term "belonging to the FT clade" shall preferably have the meaning that the proteins can be classified phylogenetically into the FT clade and/or share at least 50%, preferably 80% and most preferably 100% amino acids which are identically conserved in each of AtFT, AtTFL1, BvFT1 and BvFT2 (see amino acid columns marked with * in FIG. 10), and/or share at least 70%, preferably 80% and more preferably 90% of the amino acid sequence chain within any of the proteins AtFT, AtTFL1, BvFT1 and BvFT2.

Moreover, the inventors found the motive "APDIIDS" (SEQ ID NO: 12), and even more the motive "NAPDIIDS" (SEQ ID NO: 10) contributing to flower repressing properties of the said and related peptides and proteins, and therefore found for the first time that the potato gene StSP5G (from *Solanum tuberosum*) which is reported until now to be a potential inhibitor for the tuber development in potatoes and the tomato gene SlSP5G (from *Solanum lycopersicum*) as well as proteins derived thereof, play an important role in the repression of flowering of potatoes and tomatoes and of transgenic plants transformed therewith.

The invention further provides nucleic acids and proteins or peptides which can be expressed by said nucleic acids, wherein the sequence of the nucleic acids is partly or fully that of one of SEQ. ID No. 1, 2, 3, and 4 (FIGS. 1 to 4), or wherein the sequence of the proteins or peptides is partly or fully that of one of SEQ. ID No. 5, 6, 7, and 8 (FIGS. 5 to 8), preferably as indicated in the dependent claims.

Moreover, any of the nucleic acid sequences of the invention can be under the control of a promoter. The promoter can be a cell specific, temporally induced promoter, originally present in tobacco plants, preferably a promoter naturally controlling the genes FT1 to FT4, thereby inducing expression of FTs in the phloem companion cells. Furthermore the promoter can be a tobacco-derived tissue specific or cell specific, over the course of time constitutive active promoter like the FD promoter (wherein FD is a co-factor of FT) which is preferentially expressed in the SAM, the tissue of floral induction.

Instead, the promoter can be derived from another plant, e.g. the cell specific, temporally induced promoter of the *Arabidopsis* FT, or that of the sucrose transporter AtSUC, both active in the phloem companion cells of source leaves. The promoter could further be a tissue specific or cell specific, over the course of time constitutive active promoter like that of the *Arabidopsis* FD, driving expression in the SAM.

Other commercially available promoters or promoters available from other sources, as well as synthetic promoters, both optionally in combination with other regulating components and specifically with enhancing components can be used as well, for example the spatial and temporal strong constitutive active, viral Cauliflower Mosaic Virus (CaMV) 35S promoter. In any case, the promoter may be constitutive, but this feature is not a necessary one.

The nucleic acids and peptides/proteins of the present invention are preferably used for an enhancement of biomass per plant/per time unit, via a modulation (deferment) of the time of flowering, or complete suppression thereof.

Subsequently, the invention is further described in terms of preferred embodiments and examples.

Identification and Phylogenetic Classification of FT Homologs from *Nicotiana tabacum*

To identify potential homologs of FT in tobacco, public sequence databases (NCBI) were screened, using the coding region of the *Arabidopsis* FT (At FT) as a BLAST query which lead to the identification of a cDNA clone (DV999455.1), which contains the entire open reading frame, as indicated by an alignment with At FT. Based on this cDNA clone, primers were designed which were subsequently used for several PCR approaches using tobacco leaf cDNA and genomic DNA. In doing so, the open reading frames and the genomic sequences of four potential FT-homologs could be identified, which were designated as Nt FT1-4; the nucleic acid sequence of which is indicated in SEQ ID Nos. 1 to 4 (see FIGS. 1 to 4). An alignment of the genomic and cDNA sequences revealed the exon-intron structure of Nt FT1-4, as indicated in FIG. 9A. This Figure indicates the classification of the tobacco FT-homologs Nt FT1-4. As evident from Part (A), the exon-intron structure of tobacco Nt FT1-4 resembles that of At FT. Exons are indicated as boxes whereas lines represent introns. Dashed lines indicate introns of unknown size. Part (B) depicts the phylogenetic tree of the plant PEBP-family defined by Karlgren et al. (2011) including the identified tobacco FT-homologs NtFT1-4. The meaning of the abbreviations is as follows: ATC: *A. thaliana* Centroradialis; BFT: *A. thaliana* Brother of FT and TFL1; FT: *A. thaliana* Flowering Locus T; MFT: *A. thaliana* Mother of FT and TFL1; Nt CET1, 2, 4: *N. tabacum* Centroradialis-like genes from tobacco; Nt FT1-4: *N. tabacum* Flowering Locus T; TFL1: *A. thaliana* Terminal Flower 1; TSF: *A. thaliana* Twin Sister of Flowering Locus T.

As obvious from these sequences, all potential Nt FTs have a similar genomic structure among themselves and to FT genes from other species (exemplarily compared to At FT) with four exons interrupted by three introns. While the length of the exons is highly conserved the length of the introns differs among the Nt FTs.

Sequence analysis of the putative tobacco FTs revealed that they belong to the PEBP gene family, since all proteins possess the characteristic PEBP domain. To elucidate the phylogenetic relationship of the identified FT-homologs from tobacco, a maximum likelihood tree from an alignment of the four putative tobacco FTs was created, to facilitate the assignment of the tobacco FT-homologs to the three PEBP family clades (see FIG. 9B and Example 1).

Whereas the *Arabidopsis* proteins At FT, At TFL1 and At MFT target the three main clades in the expected manner, the tobacco FT-homologs cluster obviously in the FT-like clade, indicating their promoting function in flowering.

To validate the phylogenetic classification of Nt FT1-4, an amino acid sequence alignment of those putative tobacco FTs with the flower-promoting *Arabidopsis* FT as well as with the flower-inhibiting *Arabidopsis* TFL1 and its tobacco homologs CET1, CET2 and CET4 was created (FIG. 10). The potential tobacco FTs show a relative high overall sequence identity from 70% (Nt FT3 with Nt FT4) to ~89% (Nt FT1 with Nt FT3) to each other and ~62% (Nt FT2) to ~73% (Nt FT4) with At FT. In contrast, they show less sequence identity to tobacco CETs (~52%) and to the *Arabidopsis* TFL1 (~52%). A detailed list of all sequence identities obtained with EMBOSS needle is given in Table 1 below. Considering the phylogenetic tree and the sequence similarities, it becomes obvious that the putative tobacco FTs, namely Nt FT1-4, belong to the FT- rather than to the TFL1-clade.

Detection of Antagonistic Function of Tobacco FT Genes in Flowering

To assess the function of Nt FT1-4 in the regulation of flowering time, the corresponding genes were ectopically overexpressed under the control of the strong and constitutive cauliflower mosaic virus 35S promoter (35S:Nt FT) in tobacco. After agrobacteria mediated transformation up to 7 independent transgenic lines for each construct were regenerated.

In tobacco tissue culture, the inventors found that the 35S:Nt FT4 construct strongly accelerates flowering and overexpression causes flowers and flower-like structures in a very early stage of plant development. This can be derived from FIGS. 11A and 11B: The photographs (A) and (B) show shoots of plants wherein the coding region of Nt FT4 was cloned downstream of the constitutive promoter of the cauliflower mosaic virus (35S) and introduced into tobacco by *Agrobacterium*-mediated transformation. Only shoots with flower-like structures could be regenerated, while shoots arrested in development and did not form roots, thereby abolishing the regeneration of mature plants. Therefore, they could not regenerate to mature plants. The phenotype was nearly identical to that caused by the overexpression of the *Arabidopsis* FT (35S:At FT), which served as a control in this experiment (FIGS. 11C and 11D).

Figure 12:
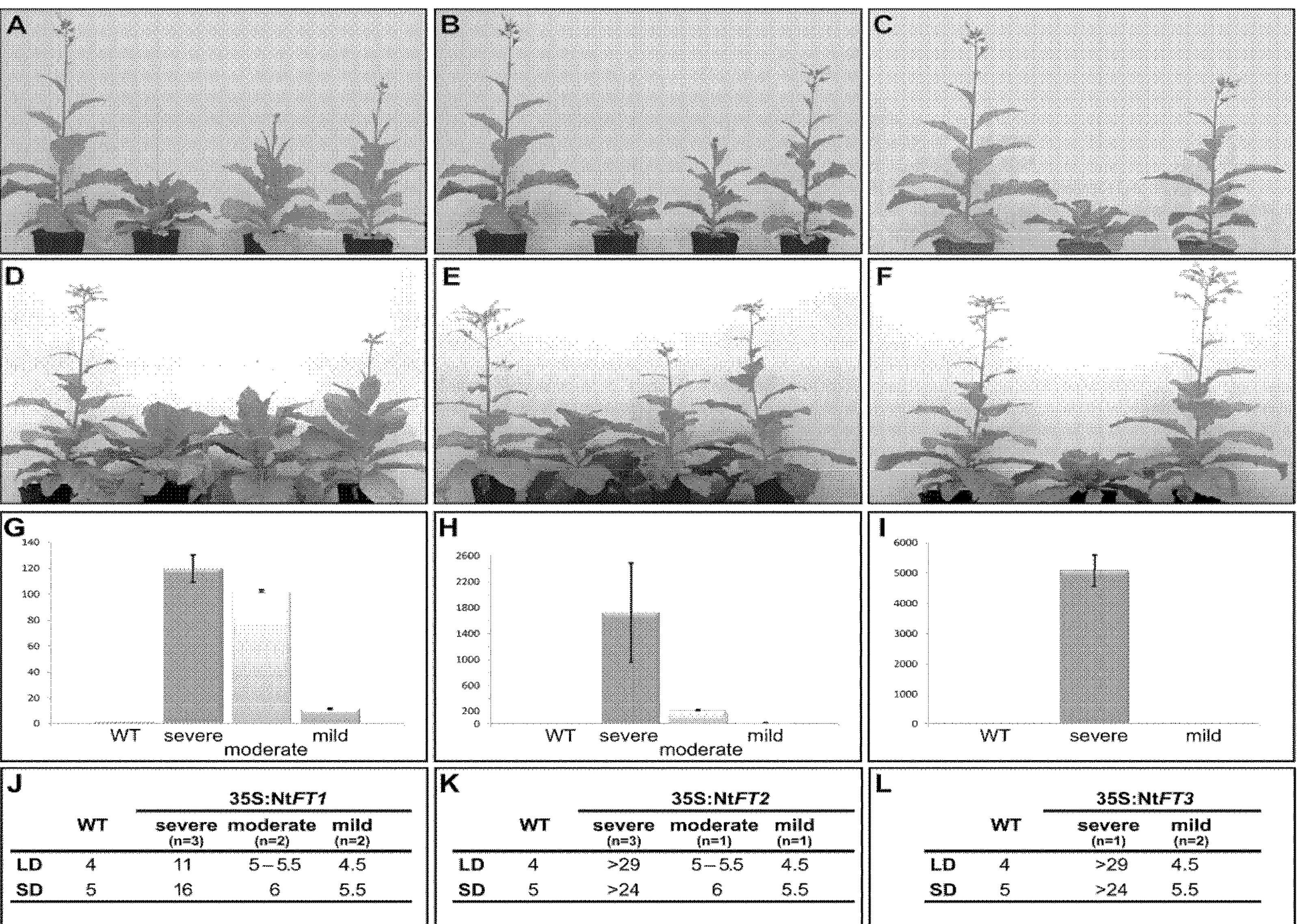
As shown in FIGS. 12A to 12F, representative transgenic tobacco lines overexpressing Nt FT1 (A, D), Nt FT2 (B, E) or Nt FT3 (C, F) were grown under long- (A to C) or short-day (D to F) conditions.
FIGS. 12G to 12I indicate that the phenotypic severity of growth behavior and flowering time positively correlates with the expression level of the corresponding transgene, while the graphs of FIGS. 12J to 12L show the results of a qRT-PCR where the WT expression level was set as 1 and the mean values of all lines representing each of the three phenotypic classes are shown.

In contrast, transformants of the constructs 35S:Nt FT1, 35S:Nt FT2 and 35S:Nt FT3 developed almost normal shoots in tissue culture. Plantlets of all three constructs with different expression levels were propagated by cuttings (in order to get two clones of each line with identical expression levels) and cultured in tissue culture until plantlets developed roots. Afterwards, transgenic clones of each line were transferred to phytotrons with one clone cultivated under LD (long day) and the other under SD (short day) conditions and flowering time was measured. Under these conditions, co-cultivated wild-type control plants started to produce flowers after four (LD) and five (SD) weeks indicating that flowering was delayed under SD. In the same LD/SD cultivation experiment, Nt FT1, Nt FT2 or Nt FT3-transgenic plants developed differentially and exhibited mild, moderate and severe phenotypes with respect to flowering time and growths under both cultivation conditions. This could be observed as shown in FIGS. 12 A to 12 F: Representative transgenic tobacco lines overexpressing Nt FT1 (A, D), Nt FT2 (B, E) or Nt FT3 (C, F) were grown under long- (A to

TABLE 1

| | AtTFL1 | NtFT1 | NtFT2 | NtFT3 | NtFT4 | CET1 | CET2 | CET4 | BvFT1 | BvFT2 |
|---|---|---|---|---|---|---|---|---|---|---|
| AtFT1 | 55 | 64.2 | 61.7 | 62.6 | 72.7 | 53.4 | 56.5 | 55.4 | 69.8 | 75.4 |
| | (72.2) | (76.5) | (73.9) | (76) | (83.5) | (72.2) | (71.8) | (71.2) | (79.9) | (87.4) |
| | AtTFL1 | 50.5 | 52.2 | 52.2 | 54.7 | 61.2 | 70.2 | 69.1 | 51.9 | 56.7 |
| | | (67.4) | (66.8) | (67.9) | (69.9) | (81.5) | (87.6) | (87.1) | (69.6) | (73.9) |
| | | NtFT1 | 87 | 89.3 | 72.5 | 49.7 | 53.3 | 51.1 | 63.9 | 69.8 |
| | | | (92.1) | (97.2) | (82.6) | (69.8) | (69.8) | (69.8) | (75.4) | (82.1) |
| | | | NtFT2 | 83.1 | 70.8 | 49.7 | 51.1 | 50 | 62.8 | 68.7 |
| | | | | (91) | (79.8) | (67) | (70) | (70) | (72.7) | (79.9) |
| | | | | NtFT3 | 70.2 | 48 | 50.5 | 50 | 63.4 | 68.2 |
| | | | | | (81.5) | (68.7) | (68.1) | (68.1) | (74.3) | (79.9) |
| | | | | | NtFT4 | 52.5 | 55.6 | 54.5 | 71.7 | 77.8 |
| | | | | | | (69.5) | (70.8) | (70.2) | (81.1) | (88.6) |
| | | | | | | CET1 | 69.1 | 69.1 | 50 | 53.4 |
| | | | | | | | (82.3) | (82.3) | (67.2) | (73.3) |
| | | | | | | | CET2 | 96.6 | 55.2 | 58.8 |
| | | | | | | | | (99.4) | (70.2) | (75.1) |
| | | | | | | | | CET4 | 54.1 | 57.6 |
| | | | | | | | | | (69.6) | (74.6) |
| | | | | | | | | | BvFT1 | 81.6 |
| | | | | | | | | | | (88.3) |

C) or short-day (D to F) conditions. At the time point when wild-type (WT) plants started flowering the transgenic lines were classified into three phenotypic groups due to their growth behavior and flowering time: transgenic lines with a mild phenotype started flowering only a few days later than WT plants, in phenotypic moderate lines flowering was retarded for approximately one week. Solely for 35S:Nt FT3 construct no moderate phenotype could be observed. At the time of WT flowering, all mildly affected plants displayed a phenotype comparable to WT plants and flowering time was only slightly delayed (~3 d) whereas moderately affected plants developed first flowers 1 to 1.5 weeks later and showed a slightly reduced internode length. In contrast, severely affected plants did not produce any flowers in the same timeframe and a strong decrease in length growth caused by a significant shortening of internodes became obvious. During this growth period, the number of leaves was comparable to WT, regardless whether plants exhibit the mild, moderate or severe phenotype. Comprehensive quantitative (q) RT-PCR experiments using total leaf RNA indicated a direct correlation between the phenotype and the level of transgene expression with the highest transcript level for a given Nt FT gene found in the most severely affected plants. This can be seen from FIGS. 12 G to 12I, indicating that the phenotypic severity of growth behavior and flowering time positively correlates with the expression level of the corresponding transgene. The graphs of FIGS. 12 J to L show the results of a qRT-PCR where the WT expression level was set as 1 and the mean values of all lines representing each of the three phenotypic classes are shown. Bars represent standard deviation of the mean; in case of n=1 the bars represent standard deviation of the corresponding triplicates of the qRT-PCR. Figures (J) to (L) indicate the weeks (after transfer to phytotron) until flowering of WT and transgenic plants overexpressing either Nt FT1 (J), Nt FT2 (K) or Nt FT3 (L) under long-(LD) and short-day (SD) conditions. The sign ">" indicates that plants are still non-flowering since the denoted weeks.

Figure 13:
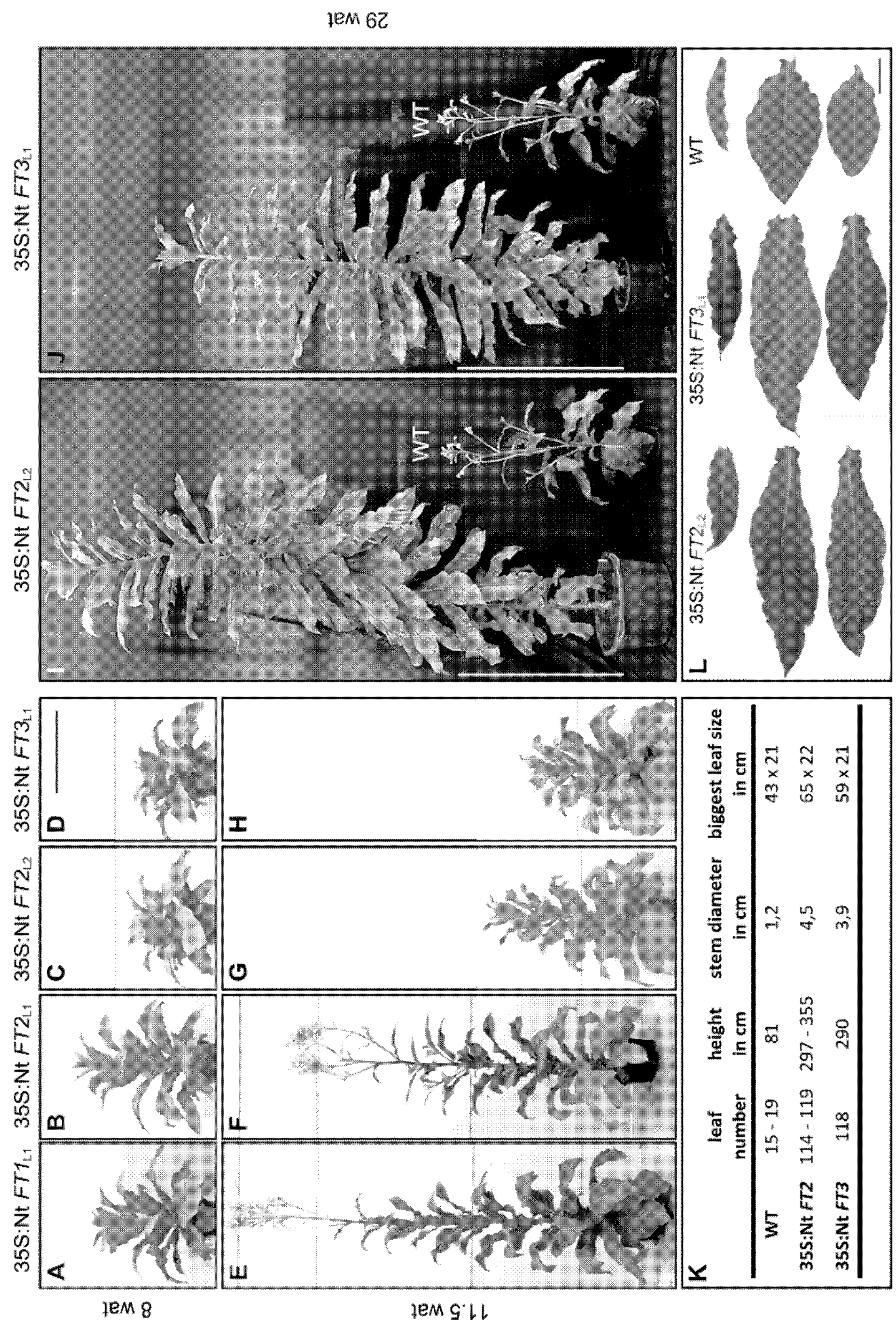
FIG. 13 indicates the growth behaviour of phenotypic severe transgenic tobacco lines overexpressing Nt FT1-3: The photographs FIGS. 13A to 13J indicate a time series of exemplarily chosen lines overexpressing Nt FT1, Nt FT2 or Nt FT3 grown under long-day conditions.

Next, it was set out to determine if flower development in severely affected plants is truly inhibited or still delayed. Therefore, all severely affected 35S:Nt FT1-3 plants were further cultivated under LD conditions in the greenhouse. FIG. 13 Indicate the growth behaviour of phenotypic severe transgenic tobacco lines overexpressing Nt FT1-3. The photographs (A) to (J) indicate a time series of exemplarily chosen lines overexpressing Nt FT1, Nt FT2 or Nt FT3 grown under long-day conditions. Pictures were taken 8, 11.5 and 29 weeks after transfer (wat) to the phytotron. The wildtype (WT) plant in I and J is 8 weeks old. The time point of bolting of the severe phenotypic lines correlates with the overexpression levels (Table 3) because plants already bolting at 8.5 wat (35S:Nt $FT1_{L1}$ and 35S:Nt $FT2_{L1}$) exhibit the lowest expression level within the severe phenotypic plants. Although plants with a compressed phenotype at 8.5 wat started bolting at around 11.5 wat they are still growing just vegetative lacking any attempts to start flower development under LD conditions. The bar on the left indicates 50 cm, the bar on the right 1 m. FIG. 13 (K) depicts a comparison of leaf number, height, stem diameter and leaf size between a flowering WT plant and the severe overexpressing tobacco lines 28 wat. Obviously, all parameters are significantly increased in the severe overexpressing lines. FIG. 13 (L) depicts a comparison of apical (top), medial (middle) and basal (bottom) leaves between 28-week-old 35S:Nt $FT2_{L2}$, 35S:Nt $FT3_{L1}$ and a flowering, 8-week-old WT plant. Bar=10 cm.

Figure 14:
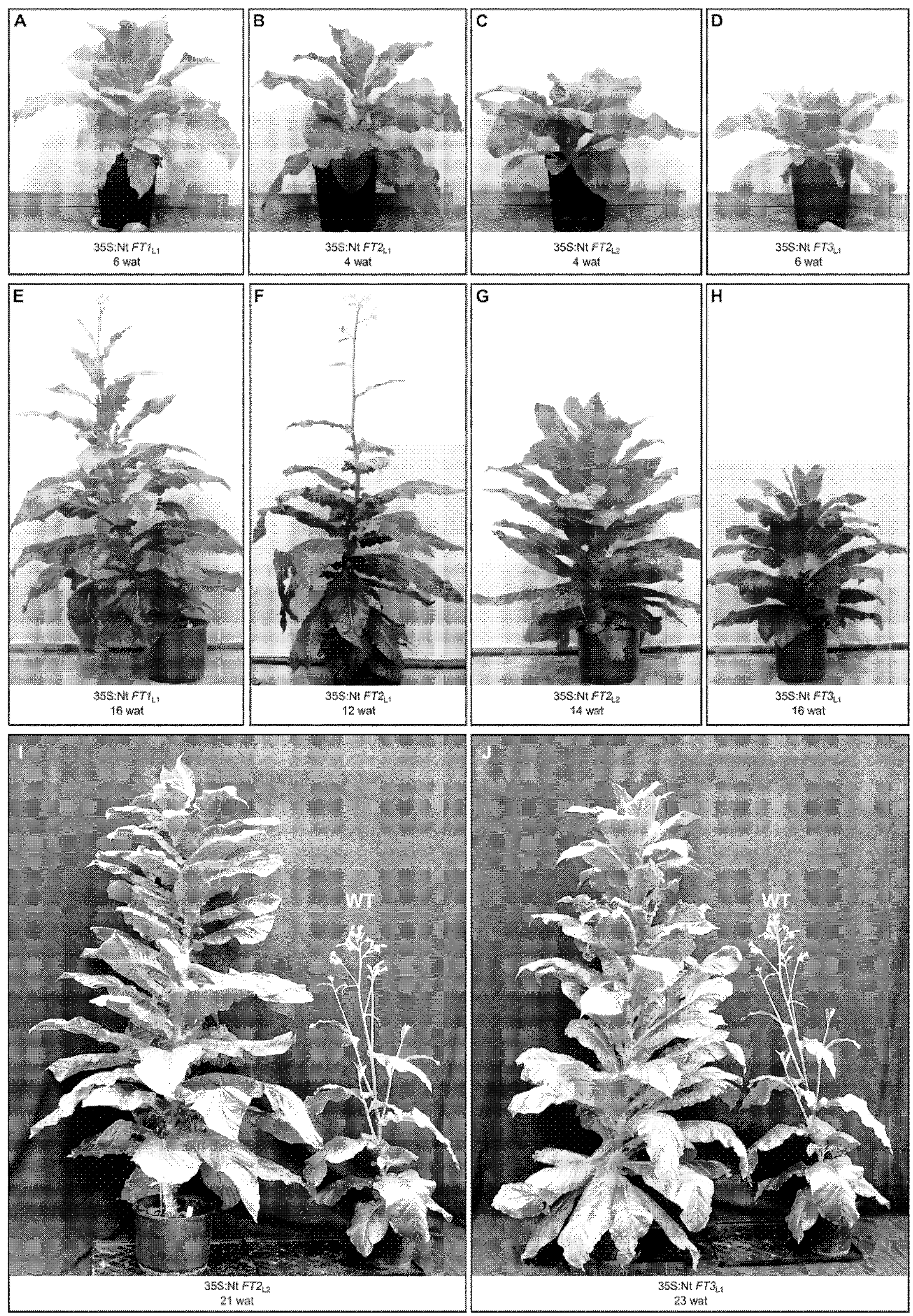
FIG. 14 depicts the growth behavior of phenotypic severe transgenic tobacco lines overexpressing Nt FT1-3 under SD conditions: Photographs (A) to (J) depict a time series of exemplarily chosen lines overexpressing Nt FT1, Nt FT2 or Nt FT3 grown under SD conditions.

All 35S:Nt FT1- and one of the 35S:Nt FT2-transgenic lines started to bolt after 6-8 weeks and consequently developed flowers at a height of approximately 2 meters after 11 weeks (exemplarily shown for one individual line in FIGS. 13A and B, E and F), while the remaining 35S:Nt FT2- and all 35S:Nt FT3-transgenic lines retained the compressed and flowerless phenotype (FIGS. 13C and 13D, 13G and 13H). Quantitative qRT-PCR experiments indicated that the Nt FT transcript level was generally higher in plants retaining the compressed phenotype (Table 3). The compressed and non-flowering 35S:Nt FT2- and all 35S:Nt FT3-transgenic lines continuously grew for more than 9 months in the greenhouse without passing the transition to the reproductive phase (FIGS. 13 I and J), which was the longest term of observation. The transgenic lines reached a size of up to 5 m, thereby displaying a tremendous increase in biomass: At the end of the experiment, they possessed ~120 leaves with a maximum size of 65 cm in length for mature leaves with an approximately 1.5 fold size increase as compared to an 8-week-old WT plant (FIGS. 13K and L). A similar increase in biomass of about 3.5 fold is also evident for the stem (FIG. 13K). It should be noted that cultivation of the severely overexpressing plants under SD conditions had to be terminated after 6 month when plants were 2 m in height and reached the ceiling of the phytotron. Until then, plants developed in the same way as their counterparts grown under LD conditions. This can be derived from FIG. 14, which depicts the growth behavior of phenotypic severe transgenic tobacco lines overexpressing Nt FT1-3 under SD conditions. Photographs (A) to (J) depict a time series of exemplarily chosen lines overexpressing Nt FT1, Nt FT2 or Nt FT3 grown under SD conditions. Pictures were taken as indicated below each image (wat: weeks after transfer to the phytotron). The wildtype plant in I and J is 8 weeks old. The time point of bolting of the severe phenotypic lines correlates with the overexpression levels (Table 3) because plants already bolting at 4 to 6 wat (35S:Nt $FT1_{L1}$ and 35S:Nt $FT2_{L1}$) exhibit the lowest expression level within the severe phenotypic plants. Although plants with a compressed phenotype at 4 to 6 wat started bolting at around 14 to 16 wat they are still growing just vegetative lacking any attempts to start flower development under SD conditions. Due to limited height within the phytotron the cultivation under SD conditions had to be stopped because plants reached the top level of the phytotron.

Detection of Basal Expression Patterns of all Nt FTs in the Leaves

Figure 15:
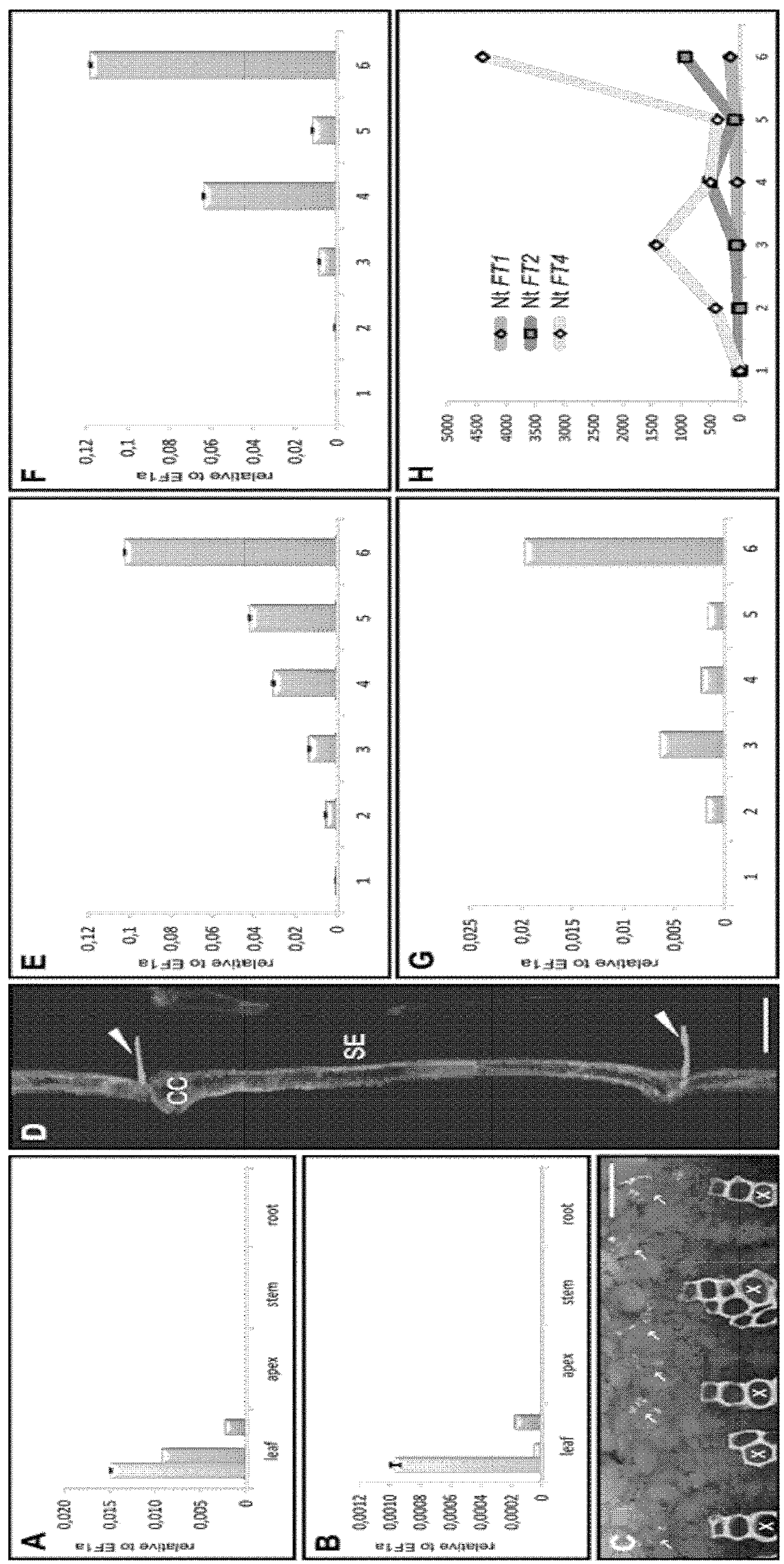
In FIGS. 15A to 15H, expression levels of the individual Nt FTs are shown in relation to Nt EF1$\alpha$, which served as the reference gene.

The spatial and temporal expression profile of the flower-repressing Nt FT1-3 and the flower-promoting Nt FT4 was analyzed. For this, total RNA from leaf, apex, stem and root tissue of 4 week-old tobacco plants cultivated under LD and SD conditions was extracted and subjected to qRT-PCR. In FIG. 15, expression levels of the individual Nt FTs are shown in relation to Nt EF1$\alpha$, which served as the reference gene. Nt FT1, Nt FT2 and Nt FT4 were exclusively expressed in leaf tissue under both light conditions, however, the level of transcription for all genes was weak and near the detection limit under LD conditions. This can be seen from FIGS. 15 A and B which indicate that Nt FT1, 2 and 4 are exclusively expressed in leaves under SD (A) as well as under LD (B) conditions, albeit the expression level under LD is near the detection limit. Values have been normalized to the transcript level of the reference gene EF1a. Although cDNA can be obtained for Nt FT3, the expression level was too low to reliably analyze its spatiotemporal expression by qRT-PCR.

To gain more insight into the locus of expression of repressing Nt FT genes, the spatial expression was studied by exemplarily expressing an ER-tagged version of the green fluorescent protein ($GFP_{ER}$) under the control of a 1-kb promoter fragment of Nt FT3 ($P_{Nt\ FT3}$).

Five independent transgenic tobacco lines were obtained by Agrobacteria-mediated plant transformation and designated as $P_{Nt\ FT3}$:$GFP_{ER}$. The ER-tagged version of GFP was chosen to prevent diffusion of GFP via the phloem in order to correctly identify GFP expressing cells. FIGS. 15 (C) and (D) show the localization of Nt FT3 expression by confocal laser scanning microscopy CLSM. 1 kb of the Nt FT3 promoter was cloned upstream of the reporter gene GFP-ER and stably transformed into tobacco plants by *Agrobacterium*-mediated transformation. The CLSM showed that GFP expression was restricted to the vascular bundle of leaves as shown by a cross section of a leaf petiole in FIG. 15 (C). The strongest signal could be observed in the veins of basal leaves, nevertheless expression and therefore fluorescence was weak, indicated by the strong autofluorescence of the xylem due to high laser intensities needed for detection. Thus, expression of Nt FT3 can be localized to the vascular bundle and more precisely to the companion cells (D, longitudinal section of a petiole). The auto-fluorescence of the xylem (X) reflects the low expression level of Nt FT3. Arrows in (C) indicate vascular bundles. Arrow heads in (D) mark sieve plates stained with aniline-blue. CC: companion cell; SE: sieve element; Bars=50 μm. As obvious from the longitudinal section of the petiole, $P_{Nt\ FT3}$ could be shown at the cellular level to be active in phloem companion cells (CCs), which are typically localized adjacent to sieve elements (SEs), whose sieve plates were stained with the callose-staining dye aniline blue (FIG. 15D). Thus $P_{Nt\ FT3}$-activity mirrors the leaf-specific expression of Nt FT1, Nt FT2 and Nt FT4, thereby indicating a common spatial expression pattern of both FTs with activating and repressing function.

Next, the temporal expression pattern of the Nt FTs was analyzed in more detail by comparing the expression levels during various developmental stages. For this reason, total RNA from tobacco seedlings and basal leaves harvested weekly until flowering from tobacco plants cultivated under LD as well as SD conditions was used to estimate expression of Nt FT1-4 by qRT-PCR As can be seen from FIGS. 15(E) to 15(G), the expression levels of Nt FT1 (E), Nt FT2 (F) and Nt FT4 (G) increase gradually during development under SD conditions showing the lowest expression level in seedlings (time point 1) and the highest expression level in leaves of flowering plants (time point 6). Transcript levels were determined in seedlings (time point 1) and basal leaves which were harvested every week until opening of the first flowers (time point 2-6). Values have been normalized to the transcript level of the reference gene EF1a.

As already noticed by analyzing the spatial expression pattern, the expression level of Nt FT3 under SD and LD as well as expression levels of the remaining Nt FTs under LD were near to the detection limit. For Nt FT1, Nt FT2 and Nt FT4 similar expression pattern under SD conditions were observed: All genes displayed quite low expression in seedlings, but a successive increase was evident during developmental stages and expression levels of all Nt FTs reached the maximum at the time point of flowering, a fact which appears to be also evident for Nt FT3. Although Nt FT4 seemed to exhibit a generally lower expression level than Nt FT1 and Nt FT2, the increase in Nt FT4 expression (4400 fold) significantly exceeded the increase of Nt FT1 (164 fold) and Nt FT2 (936 fold) expression at the time point of flowering. FIG. 15 (H) visualizes the increase of the expression levels. The values of the time points 2-6 of each gene were referred to time point 1 (set as 1 for each gene). Apparently, the expression level of Nt FT4 (encoding for a floral activator) increases to a much higher fold than that of Nt FT1 or Nt FT4 (encoding for floral repressors). As already described for several species like *Arabidopsis* or rice, FT-expression is regulated in a photoperiod dependent manner. Due to the fact that the expression of the tobacco FTs was hardly detectable under LD conditions but increased gradually under SD conditions, it can be concluded that FT expression in tobacco is also photoperiod dependent and that flowering under SD conditions is regulated in an FT-dependent manner. The molecular basis of floral induction under LD conditions, however, remains elusive. Due to missing sequence data, it cannot finally be clarified yet if flower induction under LD conditions occurs FT-independent or if further FT orthologs are involved.

Transferability of the Flower Repressing Function of NtFT1-3 on Other Plant Species To elucidate whether the flower-repressing function of Nt FTs is in principle applicable to other species, 35S:Nt FT2 was exemplarily overexpressed in the model plant *Arabidopsis*, a member of the Brassicaceae and a plant that does not possess FTs with repressing function in floral transition. 35S:Nt FT2 transgenic *Arabidopsis* plants were obtained by Agrobacteria-mediated transformation and phenotypically analyzed. It became obvious by analyzing flowering time of the different transformants that the results resemble those obtained from overexpression of 35S:Nt FT1-3 in tobacco. Plants with a high expression level of 35S:Nt FT2 exhibit a late flowering phenotype under inductive LD conditions. This is shown in FIGS. 16A to 16C. Whereas WT *Arabidopsis* plants normally flowered ~8 weeks after germination (FIG. 16A), transformants exhibiting the severe phenotype flowered ~1-2 weeks later (exemplarily shown for Nt $FT2_{L2}$ in FIG. 16B). Thus, overexpression of Nt FT2 in *Arabidopsis* also delays flowering. Further, it results in an increase of biomass (C): Plants were grown under inductive long-day conditions and pictures were taken at the time point when wild-type control plants started flowering (A and C) and one week later (B). Although not as much impressive as in tobacco, it is evident that also *Arabidopsis* plants strongly overexpressing Nt FT2 show an increase in biomass, characterized by an increase in leave size, leave number and stem diameter (FIGS. 16B and 16C).

Figures 16, 17:
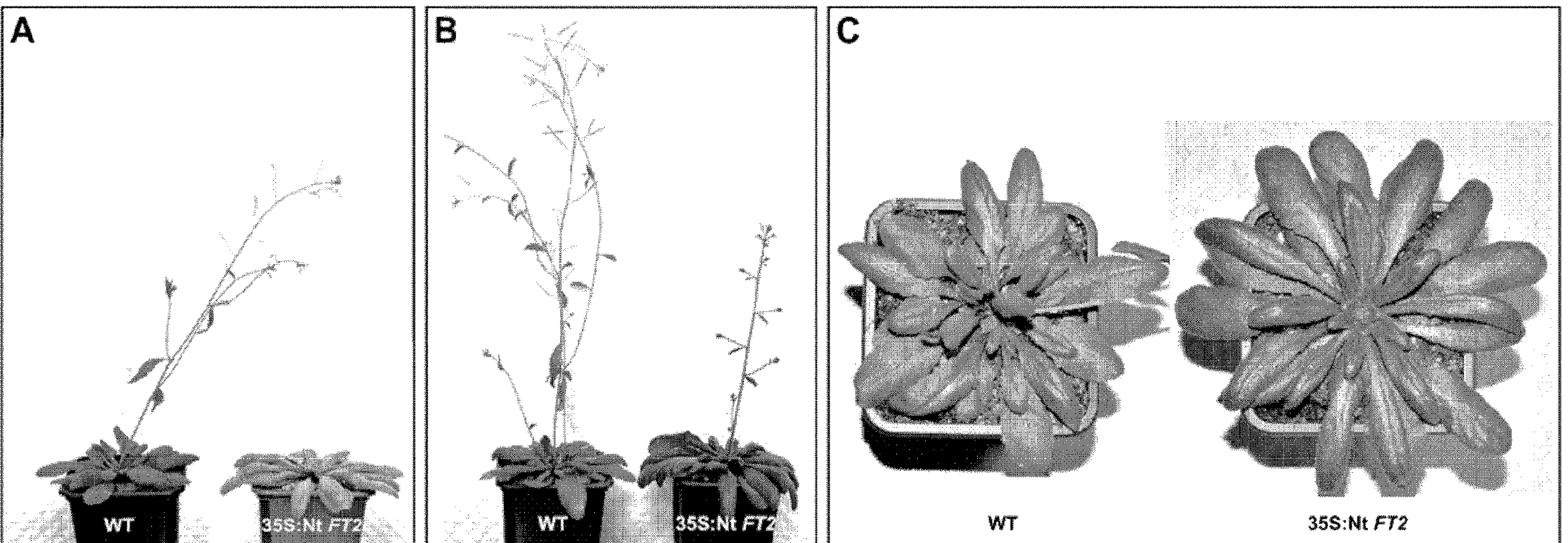
In FIG. 17, the motif NAPDIIDS of the tobacco FT with repressing function (NtFT1) was replaced by YAPGW of the tobacco FT with activating function (NtFT4) by site directed mutagenesis.

Further, 35S:Nt FT1-3 were overexpressed in the potato variety *Solanum tuberosum*. The transgenic potato plants were obtained by Agrobacteria-mediated transformation and phenotypically analyzed. It became obvious by analyzing flowering time of the different transformants that the results resemble those obtained from overexpression of 35S:Nt FT1-3 in tobacco. Plants with a high expression level of either 35S:Nt FT1, 35S:Nt FT2 or 35S:Nt FT3 exhibit a late flowering phenotype under LD conditions (FIG. 17). Whereas WT potato plants normally flowered ~8 weeks after the transfer to the greenhouse (FIG. 17A), transformants continuously grew for more than 5 months in the greenhouse without passing the transition to the reproductive phase (FIG. 17B, exemplarily shown for 35S:Nt FT1), which was the longest term of observation. The transgenic lines reached a size of up to ~3 m, thereby displaying an increase in biomass.

Thus, floral repression mediated by a repressing Nt FT obviously works species-spanning, and the invention can be used for the transformation of other plants than tobacco as well, e.g. plants of other genera of the Solanaceae family, like the genus *Solanum* (with potato as an example) or even plants of other plant families like the Brassicacea family.

The most noticeable characteristic of Nt FT1-3 is, albeit phylogenetic clearly related to the FT-like clade, that all three proteins have flower-repressing function, therefore functionally comparable to TFL1. X-ray analysis of TFL1 and FT from *Arabidopsis* revealed two typical structural characteristics of these PEBP-family proteins: On the one hand a putative ligand-binding pocket and on the other hand an external loop (Benfield and Brady, 2000; Hanzawa et al, 2005; Ahn et al., 2006). Key amino acids in these structural features have been suggested to be important for FT- versus TFL1-function in *Arabidopsis* (Hanzawa et al., 2005; Ahn et al., 2006). There, Tyr85, located at the entrance of the binding pocket, is essential for FT-function, whereas His88 (corresponding position in TFL1) mediates TFL1-function. The second crucial amino acid is part of the 14 amino acid comprising external loop encoded by the fourth exon (Segment B), which evolved very rapidly in TFL1 orthologs but is almost invariant in FT orthologs (Ahn et al., 2006). In TFL1, an Asp144 makes a hydrogen bond with His88, whereas FT carries a glutamine at the corresponding position (Gln140), which does not interact with the Tyr85. Table 2 shows a partial sequence alignment, illustrating the crucial amino acids of both repressing and activating tobacco FTs described herein, in comparison to FT/TFL1 from *Arabidopsis*, the flower promoting BvFT2 and to the floral repressor BvFT1 as well as the flower repressors SlSP5G from *Solanum lycopersicum* and StSP5G from *Solanum tuberosum*. Asterisks on the top mark amino acids essential for At FT (Tyr85/Gln140) versus At TFL1 (His88/Asp144) function (Ahn et al., 2006). Segment B is part of exon four and encodes an external loop which evolved very rapidly in TFL1-homologs but is almost invariant in FT-homologs. Letters in italic mark the amino acids which are important for the antagonistic function of By FT1 and By FT2 (Pin et al., 2010). Regarding the amino acid sequence it becomes obvious that Nt FT1-3 as well as By FT1 contain the two critical amino acid residues (or their conserved substitution), which at the corresponding position are essential for FT-function in *Arabidopsis* (Tyr-85 and Gln-140). Therefore, these amino acids are not obligatory determining FT-function in tobacco, a fact already described for sugar beet FTs (Pin et. 2010).

TABLE 2

| | segment B | SEQ ID NO: |
|---|---|---|
| AtFT | R..LGRQTVY-APG---WRQN..IYN | 13 |
| AtTFL1 | K..KQRRVIFPNIP---SRDH..EYD | 14 |
| NtFT1 | R..LDREVVN-APDIIDSRQN..FHN | 15 |
| NtFT2 | R..LDREVVN-APDIIDSREI..FHG | 16 |
| NtFT3 | R..LTRDVVN-APDIIDSREN..FYD | 17 |
| NtFT4 | R..LGRETVY-APG---WRQN..LYN | 18 |
| SlSP5G | R..LGCDAID-APDIIDSRQN..FHN | 19 |
| StSP5G | R..LGREAIN-APDIIDSRQN..FHN | 20 |
| BvFT1 | R..LGRQTVN-APQ---QRQN..LYN | 21 |
| BvFT2 | R..LGRQTVY-APG---WRQN..LYN | 22 |

Another described crucial sequence triad (LYN, located in segment C), which is conserved in FT-homologs and therefore potentially essential for FT-function, is obviously altered in Nt FT1-3, however it is present in the floral repressor By FT1 (Table 2). The latter differs from its flower-inducing ortholog By FT2 in three amino acid residues of segment B (italic in Table 2), a substitution of these residues converts the activator into a repressor and vice versa (Pin et al., 2010). Whereas the already known Solanaceae-specific activating FT (Nt FT4) possesses at this position the same amino acids as the flower inducing At FT and By FT2, the amino acid sequence of the repressing Nt FT1-3, the repressing St SP5G and the repressor Sl SP5G significantly differs to that of the repressing By FT1, instead exhibiting a conserved insertion of the three amino acids IID. Thus, the inventors assumed a species-specific amino acid pattern for repressive versus promotive function of the FTs.

In order to verify this hypothesis, a domain swapping experiment was performed. The motiv NAPDIIDS (SEQ ID NO: 10) of the tobacco FT with repressing function (NtFT1) was replaced by YAPGW (SEQ ID NO: 9) of the tobacco FT with activating function (NtFT4) by site directed mutagenesis (FIG. 18). Thus, 35S:Nt FT1swap was overexpressed in tobacco and transgenic tobacco plants were obtained by Agrobacteria-mediated transformation and phenotypically analyzed. It was obvious that the floral repressing function was eliminated by replacing the NAPDIIDS motive (SEQ ID NO: 10), since transgenic plant flowered four weeks after the transfer to the greenhouse.

EXAMPLES

Example 1: Cloning of the Tobacco FT Homologs and Analysis of their Evolutionary Relationship To identify potential homologs of FT in tobacco, public sequence databases (NCBI) were screened using the coding region of the *Arabidopsis* FT (At FT; Gen Bank: AB027504.1) as a BLAST query. A tobacco EST clone (Gen Bank: DV999455.1) was identified which was used to design an initial primer pair located in exon 1 (amino acids 1 to 8) and exon 4 (amino acids 173-177). In order to isolate potential tobacco FTs on cDNA level total RNA was extracted from tobacco leaves using the NucleoSpin® RNA Plant kit (Macherey-Nagel) and converted into cDNA using SuperScriptII (Invitrogen) following the manufacturer's instructions. Performing PCR on cDNA or PCR techniques such as rapid amplification of cDNA ends (SMARTer RACE cDNA amplification kit; Clontech) and genome walking (GenomeWalker® Universal kit; Clontech) in order to identify the corresponding genomic sequences several PCR products could be obtained. These PCR products were excised, purified, cloned and sequenced applying routine procedures known to people skilled in the art. Sequence analysis revealed four homologs with different sequences (Nt FT1-4) that share high sequence similarity to At FT. An alignment of the genomic and cDNA sequences revealed the exon-intron structure of Nt FT1-4, which is schematically depicted in FIG. 9A. As obvious from this figure, all potential Nt FTs have a similar genomic structure among themselves and to FT genes from other species (exemplarily compared to At FT) with four exons interrupted by three introns. While the length of the exons is highly conserved the length of the introns differs among the Nt FTs.

Sequence analysis using Interproscan of the putative tobacco FT proteins revealed that they belong to the PEBP gene family, since all proteins possess the characteristic PEBP domain. A recent phylogenetic analysis of plant PEBP genes revealed the presence of three main clades: FT-like, TFL1-like and MFT-like (Chardon and Damerval, 2005). All members of the PEBP gene family encode key regulators responsible for the transition from the vegetative to reproductive phase and while genes of the FT/MFT clade promote flowering, genes of the TFL-clade repress it. To elucidate the phylogenetic relationship of the identified FT-homologs from tobacco, a maximum likelihood tree was created from an alignment of the four putative tobacco FTs, the key regulators FT, TFL1 and MFT from *Arabidopsis* and the already described TFL1-homologs CET1, CET2 and CET4 from tobacco (Amaya et al., 1999). Additionally, we included the PEBP proteins characterized by Karlgren and coworkers (Karlgren et al., 2011) and the potato PEBPs StSP3D, StSP6A, StSP5G, StSP5G-like, StSP9D, StMFT, StCEN1a and StCEN1b in the phylogenetic tree to facilitate the assignment of the tobacco FT-homologs to the three PEBP family clades (FIG. 9B). Whereas the *Arabidopsis* proteins At FT, At TFL1 and At MFT target the three main clades in the expected manner (marked in red in the phylogenetic tree), the tobacco FT-homologs (marked in green in the phylogenetic tree) cluster obviously in the FT-like clade, indicating their promoting function in flowering.

To validate the phylogenetic classification of Nt FT1-4, an amino acid sequence alignment of those putative tobacco FTs with the flower-promoting *Arabidopsis* FT as well as with the flower-inhibiting *Arabidopsis* TFL1 and its tobacco homologs CET1, CET2 and CET4 was created using T-Coffee (EMBL-EBI) (FIG. 10). The potential tobacco FTs show a relative high overall sequence identity from ~70% (Nt FT3 with Nt FT4) to ~89% (Nt FT1 with Nt FT3) to each other and ~62% (Nt FT2) to ~73% (Nt FT4) with At FT. In contrast, they show less sequence identity to tobacco CETs (~52%) and to the *Arabidopsis* TFL1 (~52%). A detailed list of all sequence identities obtained with EMBOSS needle (http://www.ebi.ac.uk/Tools/psa/emboss_needle/) is given in Table 1. Considering the phylogenetic tree and the sequence similarities, it becomes obvious that the putative tobacco FTs, namely Nt FT1-4, belong to the FT- rather than to the TFL1-clade.

Example 2: Characterization of the Molecular Function of Nt FT1-4 by Overexpression Studies in Tobacco To assess the function of Nt FT1-4 in the regulation of flowering time, we next set out to ectopically overexpress the corresponding genes under the control of the strong and constitutive cauliflower mosaic virus 35S promoter (35S:Nt FT) in tobacco. Therefore, the following cloning strategy was performed.

To obtain a binary vector carrying the hygromycin resistance gene under the control of the nos promoter the pCambia1300 was digested with Nhe I and Afl II and the coding region of the hygromycin was inserted into the Nhe I and Afl II digested pBin19 (Bevan, 1984) resulting in the binary vector pBin19 Hyg.

For cloning of the overexpression constructs of Nt FT1-4 their coding regions were amplified by PCR from cDNAs within the vector pCRII® Topo® (Invitrogen) using primers containing restriction sites as shown in Table 4. PCR products were digested to the corresponding restriction sites and cloned downstream of the constitutive Cauliflower mosaic virus promoter (35S) into the pRT104 vector (Töpfer et al., 1987). The 35S:Nt FT1-4 constructs were then excised and inserted into the Hind III digested binary vectors pCambia1300 or pBin19 Hyg resulting in pCambia1300 35S:Nt FT1 and pBin19 Hyg 35S:Nt FT2-4. As a positive control the coding region of At FT was amplified from *Arabidopsis* leaf cDNA, cloned into pCRII® Topo® (Invitrogen) and sequenced. The coding region of At FT was then amplified by PCR from the cDNA within the vector pCRII® Topo® (Invitrogen) using primers containing restriction sites as shown in Table 4 below. PCR products were digested to the corresponding restriction sites and cloned downstream of the constitutive 35S promoter into the pRT104 vector. The 35S:At FT construct was then excised and inserted into the Hind III digested binary vector pCambia1300. All binary vectors were verified by sequencing and subsequently introduced by electroporation into *Agrobacterium tumefaciens* LBA4404 (Hoekema et al., 1983). For the transformation experiments *Nicotiana tabacum* cv. SR1 plants were grown on MS medium (Murashige and Skoog, 1962) under sterile conditions (LD; 23° C., 100 μmol $m^{-2}$ $sec^{-1}$) and *Agrobacterium*-mediated transformation was performed as described in Horsch et al. (1986).

In tissue culture, it was found that the 35S:Nt FT4 construct strongly accelerates flowering and overexpression causes flowers and flower-like structures in a very early stage of plant development (FIGS. 11 A and B); shoots arrest in development and do not form roots, thereby abolishing the regeneration of mature plants. The phenotype was nearly identical to that caused by the overexpression of the *Arabidopsis* FT (35S:At FT), which served as a control in this experiment (FIGS. 11 C and D).

In contrast, transformants of the constructs 35S:Nt FT1, 35S:Nt FT2 and 35S:Nt FT3 developed almost normal shoots in tissue culture. Independent transgenic lines for each construct were regenerated (seven for 35S:Nt FT1, five for 35S:Nt FT2 and three for 35S:Nt FT3) and identical clones of all transgenic and WT tobacco plants were produced by cuttings under sterile conditions, transferred into soil after rooting and grown in phytotrons under long-day (LD; 16 h/light and 8 h/dark) or short-day (SD; 8 h/light and 16 h/dark) conditions (25° C. light, 22° C. dark, 200 μmol $m^{-2}$ $sec^{-1}$). Phenotypes (mild, moderate, severe) in regard to flowering time and growth behavior were classified at the time of flowering WT plants. Due to the limited height of the phytotrons plants cultivated under LD conditions were transferred into the green house (22-25° C. light, 20-25° C. dark; artificial lighting was switched on if natural light conditions were below 700 μmol $m^{-2}$ $sec^{-1}$) whereas the cultivation under SD conditions was stopped when plants reached the top level of the phytotron.

Under these conditions described above, co-cultivated wild-type control plants started to produce flowers after four (LD) and five (SD) weeks indicating that flowering was delayed under SD. In the same LD (FIGS. 12 A to C)/SD (FIGS. 12 D to F) cultivation experiment, Nt FT1, Nt FT2 or Nt FT3-transgenic plants developed differentially and exhibited mild, moderate and severe phenotypes with respect to flowering time and growths under both cultivation conditions. Solely for 35S:Nt FT3 construct no moderate phenotype could be observed. At the time of WT flowering, all mildly affected plants displayed a phenotype comparable to WT plants and flowering time was only slightly delayed (~3 d) whereas moderately affected plants developed first flowers 1 to 1.5 weeks later and showed a slightly reduced internode length. In contrast, severely affected plants did not produce any flowers in the same timeframe and a strong decrease in length growth caused by a significant shortening of internodes became obvious. During this growth period, the number of leaves was comparable to WT, regardless whether plants exhibit the mild, moderate or severe phenotype. Comprehensive quantitative (q) RT-PCR experiments were performed using total leaf RNA extracted using the NucleoSpin® RNA Plant kit (Macherey-Nagel) and elimination of genomic DNA was performed using DNAse I (NEB) followed by a phenol-chloroform extraction. 1 μg of total RNA was reverse transcribed with SuperScript II (Invitrogen) following the manufacturer's instructions and 1 μl cDNA was used in each quantitative real-time PCR reaction (qRT). 45 cycles followed by a melting curve were performed in a CFX 96 cycler (Biorad) using the iQ SYBR Green Supermix (Biorad). Each RT sample for Nt FT1-4 was assayed in triplicates whereas reference genes, NRT (not reverse transcribed) and NTC (non-template control) controls were assayed in duplicates. Transcript levels of the two potential reference genes EF1α and L25 (Schmidt and Delaney, 2010) were examined in each RT sample. Of these genes, EF1α was found to be the most stably expressed, and this gene was therefore used to normalize transcript levels of Nt FT1-4.

Relative expression levels were calculated using the REST-MCS software (Pfaffl et al., 2002). Primers used for qRT PCRs are shown in Table 4.

The qRT-PCRs indicated a direct correlation between the phenotype and the level of transgene expression with the highest transcript level for a given Nt FT gene found in the most severely affected plants (FIG. 12 G to I).

Next, we set out to determine if flower development in severely affected plants is truly inhibited or still delayed. Therefore, all severely affected 35S:Nt FT1-3 plants were further cultivated under LD conditions in the greenhouse (FIG. 13). All 35S:Nt FT1- and one of the 35S:Nt FT2-transgenic lines started to bolt after 6-8 weeks and consequently developed flowers at a height of approximately 2 meters after 11 weeks (exemplarily shown for one individual line in FIGS. 5 A and B, E and F), while the remaining 35S:Nt FT2- and all 35S:Nt FT3-transgenic lines retained the compressed and flowerless phenotype (FIGS. 13 C and D, G and H). Quantitative qRT-PCR experiments indicated that the Nt FT transcript level was generally higher in plants retaining the compressed phenotype (Table 3).

TABLE 3

| | | LD | | | SD | | |
|---|---|---|---|---|---|---|---|
| Line | level | bolting | flowering | 28 wat | bolting | flowering | 23/21 wat |
| 35S:Nt $FT1_{L1}$ | 131.69 | 6 | 10-11 | | 13 | 16 | |
| 35S:Nt $FT1_{L2}$ | 106.08 | 8 | 10-11 | | 13 | 17 | |
| 35S:Nt $FT2_{L1}$ | 918.41 | 6.5 | 11.5 | | 4 | 10 | |
| 35S:Nt $FT2_{L2}$ | 2749.59 | 10 | — | non-flowering | 13 | | non-flowering |
| 35S:Nt $FT2_{L4}$ | 1511.75 | 11.5 | — | non-flowering | 14 | | non-flowering |
| 35S:Nt $FT3_{L1}$ | 5088.41 | 11.5 | — | non-flowering | 17 | | non-flowering |

The compressed and non-flowering 35S:Nt FT2- and all 35S:Nt FT3-transgenic lines were continuously growing for at least 9 months (end of experiment) in the greenhouse without passing the transition to the reproductive phase (FIGS. 5 I and J). The transgenic lines reached a size of up to 5 m, thereby displaying a tremendous increase in biomass: At the end of the experiment, they possessed ~120 leaves with a maximum size of 65 cm in length for mature leaves with an approximately 1.5 fold size increase as compared to an 8-week-old WT plant (FIGS. 13 K and L). A similar increase in biomass of about 3.5 fold is also evident for the stem (FIG. 13 K).

TABLE 4

| | (with stop codon, respectively. for: forward primer; rev: reverse primer; Tm: annealing temperature) | | | |
|---|---|---|---|---|
| purpose | name | 5'-3' sequence | SEQ ID NO: | Tm |
| initial | NtFT for | ATGTCAAGACTAGATCCTTTAATAG | 23 | 56° C. |
| primer pair | NtFT rev | TTATAGGTGACGGCCAC | 24 | |
| 5'RACE | 5'RACE NtFT1 | GCAGCAACAGGCGAATTGAGATTATGAAATCTC | 25 | 75° C. |
| | 5'RACE NtFT2 | AAACAGCGGCAACAGGCAAATTGAGAC | 26 | 75° C. |
| | 5'RACE NtFT3 | CAACATCTCGAGTCAATTGTCGAAACAG | 27 | 71° C. |
| | 5'RACE NtFT4 | ACAGTTTCGCGACCCAATTGTC | 28 | 69° C. |
| 3'RACE | 3'RACE NtFT1 | AAGCAACCCAAACCTGAGGGAGTATCTG | 29 | 72° C. |
| | 3'RACE NtFT2 | CAGATATCCCTGCAACCACAGAAGCAAC | 30 | 73° C. |
| | 3'RACE NtFT3 | AATTGTCCACCAACCTAGGGTTGACGTG | 31 | 74° C. |
| | 3'RACE NtFT4 | TCACAGATATCCCAGCAACTAC | 32 | 61° C. |

TABLE 4-continued

| | (with stop codon, respectively. for: forward primer; rev: reverse primer; Tm: annealing temperature) | | | |
|---|---|---|---|---|
| purpose | name | 5'-3' sequence | SEQ ID NO: | Tm |
| qRT | qRT NtFT1 for | AAGCAACCCAAACCTGAGGGAGTATCTG | 29 | 71° C. |
| | qRT NtFT1 rev | GCAGCAACAGGCGAATTGAGATTATGAAATCTC | 25 | |
| | qRT NtFT2 for | AGATATCCCTGCAACCACAGAAGCAAC | 33 | 70° C. |
| | qRT NtFT2 rev | AAACAGCGGCAACAGGCAAATTGAGAC | 26 | |
| | qRT NtFT3 for | AATTGTCCACCAACCTAGGGTTGACGTG | 31 | 67.3° C. |
| | qRT NtFT3 rev | CATTCACAACATCTCGAGTCAATTGTCGAAACAG | 34 | |
| | qRT NtFT4 for | GATATCCCAGCAACTACAGATACAAG | 35 | 67° C. |
| | qRT NtFT4 rev | GAAACGGGCAAACCAAGATTGTAAAC | 36 | |
| | qRT EF1a for | TGAGATGCACCACGAAGCTC | 37 | 64° C. |
| | qRT EF1a rev | CCAACATTGTCACCAGGAAGTG | 38 | |
| | qRT L25 for | CCCCTCACCACAGAGTCTGC | 39 | 64° C. |
| | qRT L25 rev | AAGGGTGTTGTTGTCCTCAATCTT | 40 | |
| pRT104 | NtFT1/3 for Xho I | AGActcgagATGTCAAGACTAGATCCTTTAATAG | 41 | 55° C. |
| | NtFT2 for Xho I | AGActcgagATGTTAAGAGCAAATCCTTTAG | 42 | |
| | NtFT1-3 rev Xba I | ACAtctagaTTATAGGTGACGGCCAC | 43 | |
| | NtFT4 for Xho I | AGActcgagATGCCAAGAATAGATCCTTTG | 44 | |
| | NtFT4 rev Xba I | ACAtctagaTTAATATGCGCGGCGGCCAC | 45 | |
| | AtFT for Xho I | AGActcgagATGTCTATAAATATAAGAGACC | 46 | 50° C. |
| | AtFT rev Xba I | AGAtctagaCTAAAGTCTTCTTCCTCCGCAG | 47 | |
| pBs1029 | $P_{Nt\ FT3}$ for Kpn I | AGAggtaccTCGTAAGATTTTTAGTTTGTTC | 48 | 60° C. |
| | $P_{Nt\ FT3}$ rev Xho I | AGActcgagTTTGATGGTGTGGAAATGTTTAC | 49 | |
| pBin Hyg | $P_{Nt\ FT3}$ for Sal I | AGAgtcgacTCGTAAGATTTTTAGTTTGTTC | 50 | 58° C. |
| | 35S terminator rev Sal I | AGAgtcgacGTCACTGGATTTTGGTTTTAG | 51 | |
| pENTR4™ | AtFD for Sal I | AGAgtcgacATGTTGTCATCAGCTAAGCATC | 52 | 60° C. |
| | AtFD rev Not I - stop | AGAgcggccgcGAAAATGGAGCTGTGGAAG | 53 | |
| | AtFD rev Not I + stop | AGAgcggccgcTCAAAATGGAGCTGTGGAAG | 54 | |
| | AtFT for Sal I | AGAgtcgacATGTCTATAAATATAAGAGACC | 55 | 50° C. |
| | AtFT rev Not I - stop | AGAgcggccgcGAAAGTCTTCTTCCTCCGCAG | 56 | |
| | AtFT rev Not I + stop | AGAgcggccgcCTAAAGTCTTCTTCCTCCGCAG | 57 | |
| | NtFT1/3 for Sal I | AGAgtcgacATGTCAAGACTAGATCC | 58 | 50° C. |
| | NtFT2 for Sal I | AGAgtcgacATGTTAAGAGCAAATCC | 59 | |
| | NtFT4 for Sal I | AGAgtcgacATGCCAAGAATAGATCCTTTG | 60 | |
| | NtFT1-3 rev Not I - stop | AGAgcggccgcGATAGGTGACGGCCAC | 61 | |
| | NtFT1-3 rev Not I + stop | AGAgcggccgcCGATTATAGGTGACGGCC | 62 | |
| | NtFT4 rev Not I - stop | AGAgcggccgcccATATGCGCGGCGGCCAC | 63 | |
| | NtFT4 rev Not I + stop | AGAgcggccgcTTAATATGCGCGGCGGCCAC | 64 | |
| | mEmerald for | AGAAccatggGTAAAGGAGAAG | 65 | |
| | mEmerald rev | AGAActcgagTGTTTGTATAGTTCATCCATGCCATGT GTAATCCCAGCAGCTGTTACTCTCTCAAGAAGGAC CATGTG | 66 | |

Example 3: Gene Expression Analysis of Nt FT1-4

Next, we analyzed the spatial and temporal expression profile of the flower-repressing Nt FT1-3 and the flower-promoting Nt FT4. Therefore, tobacco seeds were sown in soil and grown in phytotrons under LD or SD conditions. For the spatial expression pattern leaves, apices, stems as well as roots of three, ~4-week-old plants were pooled and used for total RNA extraction. To examine the temporal expression levels of Nt FT1-4 seedlings were harvested determining time point 1 and then basal leaves of three plants were harvested every week until opening of the first flower resulting in 5 and 6 harvesting times in total for LD and SD conditions, respectively. Total RNA was extracted using the NucleoSpin® RNA Plant kit (Macherey-Nagel) and elimination of genomic DNA was performed using DNAse I (NEB) followed by a phenol-chloroform extraction. 1 μg of total RNA was reverse transcribed with SuperScript II (Invitrogen) following the manufacturer's instructions and 1 μl cDNA was subjected to qRT-PCR. 45 cycles followed by a melting curve were performed in a CFX 96 cycler (Biorad) using the iQ SYBR Green Supermix (Biorad). Each RT sample for Nt FT1-4 was assayed in triplicates whereas reference genes, NRT (not reverse transcribed) and NTC (non-template control) controls were assayed in duplicates. Transcript levels of the two potential reference genes EF1α and L25 (Schmidt and Delaney, 2010) were examined in each RT sample. Of these genes, EF1α was found to be the most stably expressed, and this gene was therefore used to normalize transcript levels of Nt FT1-4. Relative expression levels were calculated using the REST-MCS software (Pfaffl et al., 2002). Primers used for qRT-PCR are shown in Table 4.

In FIG. 15, expression levels of the individual Nt FTs are shown in relation to Nt EF1α, which served as the reference gene. Nt FT1, Nt FT2 and Nt FT4 were exclusively expressed in leaf tissue under both light conditions, however, the level of transcription for all genes was weak and near the detection limit under LD conditions (FIGS. 15 A and B). Although cDNA can be obtained for Nt FT3, the expression level was too low to reliably analyze its spatiotemporal expression by qRT-PCR.

To gain more insight into the locus of expression of repressing Nt FT genes, we also studied the spatial expression by exemplarily expressing an ER-tagged version of the green fluorescent protein ($GFP_{ER}$) under the control of a 1-kb promoter fragment of Nt FT3 ($P_{Nt\ FT3}$). For cloning of this construct 1 kb of the $P_{Nt\ FT3}$ was amplified using primers containing restriction sites as shown in Table 4. PCR products were digested to the corresponding restriction sites and cloned upstream of the $GFP_{ER}$ reporter gene into the pBs $GFP_{ER}$ (Noll et al., 2007). The ER-tagged version of GFP was chosen to prevent diffusion of GFP via the phloem in order to correctly identify GFP expressing cells. After verification by sequencing the cassette consisting of $P_{Nt\ FT3}$:$GPP_{ER}$ and the terminator of the cauliflower mosaic virus was amplified using primers containing Sal I restriction sites. PCR products were digested with Sal I, inserted into the Sal I digested binary vector pBin19 Hyg, verified by sequencing and subsequently introduced by electroporation into *Agrobacterium tumefaciens* LBA4404 (Hoekema et al., 1983).

Five independent transgenic tobacco lines were obtained by Agrobacteria-mediated plant transformation and designated as $P_{Nt\ FT3}$:$GFP_{ER}$. The transgenic plants were transferred into soil after rooting, grown in the green house and four to six week old plants were analyzed by confocal laser scanning microscopy (CLSM) using a Leica TCS SP5× microscope (Leica Microsystems, Germany) with excitation/emission wavelengths of 488/500-600 nm.

The CLSM analysis showed that GFP expression was restricted to the vascular bundle of leaves as shown by a cross section of a leaf petiole in FIG. 15 C. The strongest signal could be observed in the veins of basal leaves, nevertheless expression and therefore fluorescence was weak, indicated by the strong autofluorescence of the xylem due to high laser intensities needed for detection. As obvious from the longitudinal section of the petiole, $P_{Nt\ FT3}$ could be shown at the cellular level to be active in phloem companion cells (CCs), which are typically localized adjacent to sieve elements (SEs), whose sieve plate were stained with the callose-staining dye aniline blue (FIG. 15 D). Thus $P_{Nt\ FT3}$-activity mirrors the leaf-specific expression of Nt FT1, Nt FT2 and Nt FT4, thereby indicating a common spatial expression pattern of both FTs with activating and repressing function.

Next we set out to analyze the temporal expression pattern of the Nt FTs in more detail by comparing the expression levels during various developmental stages. For this reason, total RNA from tobacco seedlings and basal leaves harvested weekly until flowering from tobacco plants cultivated under LD as well as SD conditions was used to estimate expression of Nt FT1-4 by qRT-PCR (FIGS. 15 E to G). Although Nt FT4 seemed to exhibit a generally lower expression level than Nt FT1 and Nt FT2, the increase in Nt FT4 expression (4400 fold) significantly exceeded the increase of Nt FT1 (164 fold) and Nt FT2 (936 fold) expression (FIG. 7 H) at the time point of flowering.

Example 4: Nt FT2 Also Represses Flowering in *Arabidopsis*

To elucidate whether the flower-repressing function of Nt FTs is in principle applicable to other species, we exemplarily overexpressed 35S:Nt FT2 in the model plant *Arabidopsis*, a member of the Brassicaceae and a plant that does not possess FTs with repressing function in floral transition. For the overexpression of Nt FT2 in *Arabidopsis* the 35S:Nt FT2 construct was inserted into the Hind III digested binary vector plab12.1 carrying the BASTA resistance gene under the control of mannopine synthase promoter (Post et al., 2012). All binary vectors were verified by sequencing and subsequently introduced by electroporation into *Agrobacterium tumefaciens* LBA4404 (Hoekema et al., 1983). For the overexpression studies in *Arabidopsis* seeds of *A. thaliana* Col were sown in soil and cultivated under LD conditions in the phytotron (23° C. light, 17° C. night and 100 μmol $m^{-2}$ $sec^{-1}$). Transgenic *Arabidopsis* plants were generated by the floral dip method (Clough and Bent, 1998). Seeds of transformed *Arabidopsis* plants were sown in soil and sprayed with BASTA after germination to select for positive transgenic plants.

It became obvious by analyzing flowering time of the different transformants that the results resemble that obtained from overexpression of 35S:Nt FT1-3 in tobacco. Plants with a high expression level of 35S:Nt FT2 exhibit a late flowering phenotype under inductive LD conditions (FIGS. 16 A to C). Whereas WT *Arabidopsis* plants normally flowered ~8 weeks after germination (FIG. 16 A), transformants exhibiting the severe phenotype flowered ~1-2 weeks later (exemplarily shown for Nt $FT2_{L2}$ in FIG. 16 B). Although not as much impressive as in tobacco, also *Arabidopsis* plants strongly overexpressing Nt FT2 showed an increase in biomass, characterized by an increase in leave size, leave number and stem diameter (FIGS. 16 B and C).

SEQUENCE LISTING

```
<160> NUMBER OF SEQ ID NOS: 83

<210> SEQ ID NO 1
<211> LENGTH: 534
<212> TYPE: DNA
<213> ORGANISM: Nicotiana tabacum

<400> SEQUENCE: 1

atgtcaagac tagatccttt aatagtatct ggggtaatag gagatgtttt ggattcattt     60

acaaggtcta tagactttag tgtggtttat aataataggg tacaagtcta caatggttgt    120

ggtttgaggc cttcacaaat tgtcaaccaa cctagggttg acattggagg agatgatctt    180
```

```
cgcacttttt acactatggt tatggtggat ccagatgctc caacccccaag caacccaaac    240

ctgagggagt atctgcactg gctggtcaca gatatcccag caaccacagg agcaaacttt    300

ggcaatgaaa ttatacgata cgagagtcca cgaccttcac tgggaattca tcgctatatt    360

ttcgtgttgt ttcagcaatt ggatcgagag gttgtgaatg ctcctgatat aattgattct    420

cgtcagaatt ttaacacaag agactttgcg agatttcata atctcaattc gcctgttgct    480

gctgtttact tcaattgcaa tagagaaggt ggtaccggtg gccgtcacct ataa          534


<210> SEQ ID NO 2
<211> LENGTH: 534
<212> TYPE: DNA
<213> ORGANISM: Nicotiana tabacum

<400> SEQUENCE: 2

atgttaagag caaatccttt agtagtatct ggtgtaatag gagatgtatt ggatccattt     60

acaaagtctg tagactttga tgtggtttac aataataatg tgcaggtcta caatggctgt    120

ggattgaggc cttcacaaat tgtcaaccaa cctagggttg acattgcagg agatgatttt    180

cgcacttttt acactctggt tatggtggat ccagatgctc caaccccgag caacccaaat    240

ctgagggagt atctccattg gctggtcaca gatatccctg caaccacaga agcaaccttt    300

ggcaatgaaa ttgtaagtta tgagagacca caaccttcat tgggaattca tcgctatatt    360

ttcgtgttgt ttcggcaatt ggatcgagag gttgtgaatg ctcctgatat aattgattct    420

cgtgagattt ttaacactag agactttgca aggtttcacg gtctcaattt gcctgttgcc    480

gctgtttact tcaattgcaa tagggaaggc ggtaccggtg gccgtcacct ataa          534


<210> SEQ ID NO 3
<211> LENGTH: 534
<212> TYPE: DNA
<213> ORGANISM: Nicotiana tabacum

<400> SEQUENCE: 3

atgtcaagac tagatccttt aatagtatct ggtgttatag gagatgtatt ggatccattt     60

acaaggtcta tagactttaa tgttgtttac aataatagga tgcaagtcta caatggctgt    120

ggtttgaggc cttcacaaat tgtccaccaa cctagggttg acgtgggagg agatgatctt    180

cgcacttttt acactctggt tatggtggat ccagatgctc caaccccgag caatccaaac    240

cagagggagt atctccactg gctggtcaca aatatcccag caaccacagg agcacacttc    300

gggaatgaaa ttatacaata cgagagtcca cgaccttcat tgggaattca tcgctatatt    360

tttgtgctgt ttcgacaatt gactcgagat gttgtgaatg ctcctgatat aattgattct    420

cgtgagaatt ttaacacaag agactttgca aggttttacg atctcaattc gcctgttgct    480

gctatgtact tcaatagcaa tagggaaagt ggtactggtg gccgtcacct ataa          534


<210> SEQ ID NO 4
<211> LENGTH: 525
<212> TYPE: DNA
<213> ORGANISM: Nicotiana tabacum

<400> SEQUENCE: 4

atgccaagaa tagatccttt gatagttggt cgtgtggtag gagatgtttt agatccattc     60

acaaggtctg ttgatcttag agtggtttac aataataggg aagtcaacaa tgcatgtggc    120

ttgaaacctt ctcaaattgt tacgcaacct agggttcaaa ttggagggga tgatcttcgc    180

aacttttaca ctctggttat ggtggatcct gatgctccaa gcccaagcaa ccctaacctg    240
```

```
agggagtatc tacactggct ggtcacagat atcccagcaa ctacagatac aagctttgga    300

aatgaagtta tatgctacga gaatccacaa ccatcattgg gaattcatcg ctttgttttc    360

gtgttgtttc gacaattggg tcgcgaaact gtgtatgcac caggttggcg tcagaatttc    420

agcacaagag actttgcaga agtttacaat cttggtttgc ccgtttctgc tgtttacttc    480

aattgccata gggagagtgg tactggtggc cgccgcgcat attaa                    525


<210> SEQ ID NO 5
<211> LENGTH: 177
<212> TYPE: PRT
<213> ORGANISM: Nicotiana tabacum

<400> SEQUENCE: 5

Met Ser Arg Leu Asp Pro Leu Ile Val Ser Gly Val Ile Gly Asp Val
1               5                   10                  15

Leu Asp Ser Phe Thr Arg Ser Ile Asp Phe Ser Val Val Tyr Asn Asn
            20                  25                  30

Arg Val Gln Val Tyr Asn Gly Cys Gly Leu Arg Pro Ser Gln Ile Val
        35                  40                  45

Asn Gln Pro Arg Val Asp Ile Gly Gly Asp Asp Leu Arg Thr Phe Tyr
    50                  55                  60

Thr Met Val Met Val Asp Pro Asp Ala Pro Thr Pro Ser Asn Pro Asn
65                  70                  75                  80

Leu Arg Glu Tyr Leu His Trp Leu Val Thr Asp Ile Pro Ala Thr Thr
                85                  90                  95

Gly Ala Asn Phe Gly Asn Glu Ile Ile Arg Tyr Glu Ser Pro Arg Pro
            100                 105                 110

Ser Leu Gly Ile His Arg Tyr Ile Phe Val Leu Phe Gln Gln Leu Asp
        115                 120                 125

Arg Glu Val Val Asn Ala Pro Asp Ile Ile Asp Ser Arg Gln Asn Phe
    130                 135                 140

Asn Thr Arg Asp Phe Ala Arg Phe His Asn Leu Asn Ser Pro Val Ala
145                 150                 155                 160

Ala Val Tyr Phe Asn Cys Asn Arg Glu Gly Gly Thr Gly Gly Arg His
                165                 170                 175

Leu


<210> SEQ ID NO 6
<211> LENGTH: 177
<212> TYPE: PRT
<213> ORGANISM: Nicotiana tabacum

<400> SEQUENCE: 6

Met Leu Arg Ala Asn Pro Leu Val Val Ser Gly Val Ile Gly Asp Val
1               5                   10                  15

Leu Asp Pro Phe Thr Lys Ser Val Asp Phe Asp Val Val Tyr Asn Asn
            20                  25                  30

Asn Val Gln Val Tyr Asn Gly Cys Gly Leu Arg Pro Ser Gln Ile Val
        35                  40                  45

Asn Gln Pro Arg Val Asp Ile Ala Gly Asp Asp Phe Arg Thr Phe Tyr
    50                  55                  60

Thr Leu Val Met Val Asp Pro Asp Ala Pro Thr Pro Ser Asn Pro Asn
65                  70                  75                  80

Leu Arg Glu Tyr Leu His Trp Leu Val Thr Asp Ile Pro Ala Thr Thr
                85                  90                  95
```

```
Glu Ala Thr Phe Gly Asn Glu Ile Val Ser Tyr Glu Arg Pro Gln Pro
            100                 105                 110

Ser Leu Gly Ile His Arg Tyr Ile Phe Val Leu Phe Arg Gln Leu Asp
        115                 120                 125

Arg Glu Val Val Asn Ala Pro Asp Ile Ile Asp Ser Arg Glu Ile Phe
    130                 135                 140

Asn Thr Arg Asp Phe Ala Arg Phe His Gly Leu Asn Leu Pro Val Ala
145                 150                 155                 160

Ala Val Tyr Phe Asn Cys Asn Arg Glu Gly Gly Thr Gly Gly Arg His
                165                 170                 175

Leu


<210> SEQ ID NO 7
<211> LENGTH: 177
<212> TYPE: PRT
<213> ORGANISM: Nicotiana tabacum

<400> SEQUENCE: 7

Met Ser Arg Leu Asp Pro Leu Ile Val Ser Gly Val Ile Gly Asp Val
1               5                   10                  15

Leu Asp Pro Phe Thr Arg Ser Ile Asp Phe Asn Val Val Tyr Asn Asn
            20                  25                  30

Arg Met Gln Val Tyr Asn Gly Cys Gly Leu Arg Pro Ser Gln Ile Val
        35                  40                  45

His Gln Pro Arg Val Asp Val Gly Gly Asp Asp Leu Arg Thr Phe Tyr
    50                  55                  60

Thr Leu Val Met Val Asp Pro Asp Ala Pro Thr Pro Ser Asn Pro Asn
65                  70                  75                  80

Gln Arg Glu Tyr Leu His Trp Leu Val Thr Asn Ile Pro Ala Thr Thr
                85                  90                  95

Gly Ala His Phe Gly Asn Glu Ile Ile Gln Tyr Glu Ser Pro Arg Pro
            100                 105                 110

Ser Leu Gly Ile His Arg Tyr Ile Phe Val Leu Phe Arg Gln Leu Thr
        115                 120                 125

Arg Asp Val Val Asn Ala Pro Asp Ile Ile Asp Ser Arg Glu Asn Phe
    130                 135                 140

Asn Thr Arg Asp Phe Ala Arg Phe Tyr Asp Leu Asn Ser Pro Val Ala
145                 150                 155                 160

Ala Met Tyr Phe Asn Ser Asn Arg Glu Ser Gly Thr Gly Gly Arg His
                165                 170                 175

Leu


<210> SEQ ID NO 8
<211> LENGTH: 174
<212> TYPE: PRT
<213> ORGANISM: Nicotiana tabacum

<400> SEQUENCE: 8

Met Pro Arg Ile Asp Pro Leu Ile Val Gly Gly Val Val Gly Asp Val
1               5                   10                  15

Leu Asp Leu Phe Thr Arg Ser Val Asp Leu Arg Val Val Tyr Asn Asn
            20                  25                  30

Lys Glu Val Asn Asn Ala Cys Gly Leu Lys Pro Ser Gln Ile Val Thr
        35                  40                  45

Gln Pro Arg Val Gln Ile Gly Gly Asp Asp Leu Arg Asn Phe Tyr Thr
    50                  55                  60
```

```
Leu Val Met Val Asp Pro Asp Ala Pro Ser Pro Ser Asn Pro Asn Leu
65                  70                  75                  80

Arg Glu Tyr Leu His Trp Leu Val Thr Asp Ile Pro Ala Thr Thr Asp
                85                  90                  95

Thr Ser Phe Gly Asn Glu Val Val Cys Tyr Glu Ser Pro Gln Pro Ser
            100                 105                 110

Met Gly Ile His Arg Phe Val Phe Ala Leu Phe Arg Gln Leu Gly Arg
        115                 120                 125

Glu Thr Val Tyr Ala Pro Gly Trp Arg Gln Asn Phe Asn Thr Arg Asp
    130                 135                 140

Phe Ala Glu Leu Tyr Asn Leu Gly Leu Pro Val Ala Ala Val Tyr Phe
145                 150                 155                 160

Asn Cys His Arg Glu Ser Gly Thr Gly Gly Arg Arg Ala Tyr
                165                 170


<210> SEQ ID NO 9
<211> LENGTH: 5
<212> TYPE: PRT
<213> ORGANISM: Unknown
<220> FEATURE:
<223> OTHER INFORMATION: Description of Unknown:
      PEBP family peptide motif sequence

<400> SEQUENCE: 9

Tyr Ala Pro Gly Trp
1               5


<210> SEQ ID NO 10
<211> LENGTH: 8
<212> TYPE: PRT
<213> ORGANISM: Unknown
<220> FEATURE:
<223> OTHER INFORMATION: Description of Unknown:
      PEBP family peptide motif sequence

<400> SEQUENCE: 10

Asn Ala Pro Asp Ile Ile Asp Ser
1               5


<210> SEQ ID NO 11
<211> LENGTH: 5
<212> TYPE: PRT
<213> ORGANISM: Unknown
<220> FEATURE:
<223> OTHER INFORMATION: Description of Unknown:
      PEBP family peptide motif sequence

<400> SEQUENCE: 11

Asn Ala Pro Gln Gln
1               5


<210> SEQ ID NO 12
<211> LENGTH: 7
<212> TYPE: PRT
<213> ORGANISM: Unknown
<220> FEATURE:
<223> OTHER INFORMATION: Description of Unknown:
      PEBP family peptide motif sequence

<400> SEQUENCE: 12

Ala Pro Asp Ile Ile Asp Ser
1               5
```

<210> SEQ ID NO 13
<211> LENGTH: 14
<212> TYPE: PRT
<213> ORGANISM: Arabidopsis thaliana

<400> SEQUENCE: 13

```
Leu Gly Arg Gln Thr Val Tyr Ala Pro Gly Trp Arg Gln Asn
1               5                   10
```

<210> SEQ ID NO 14
<211> LENGTH: 15
<212> TYPE: PRT
<213> ORGANISM: Arabidopsis thaliana

<400> SEQUENCE: 14

```
Lys Gln Arg Arg Val Ile Phe Pro Asn Ile Pro Ser Arg Asp His
1               5                   10                  15
```

<210> SEQ ID NO 15
<211> LENGTH: 17
<212> TYPE: PRT
<213> ORGANISM: Nicotiana tomentosiformis

<400> SEQUENCE: 15

```
Leu Asp Arg Glu Val Val Asn Ala Pro Asp Ile Ile Asp Ser Arg Gln
1               5                   10                  15

Asn
```

<210> SEQ ID NO 16
<211> LENGTH: 17
<212> TYPE: PRT
<213> ORGANISM: Nicotiana tomentosiformis

<400> SEQUENCE: 16

```
Leu Asp Arg Glu Val Val Asn Ala Pro Asp Ile Ile Asp Ser Arg Glu
1               5                   10                  15

Ile
```

<210> SEQ ID NO 17
<211> LENGTH: 17
<212> TYPE: PRT
<213> ORGANISM: Nicotiana tomentosiformis

<400> SEQUENCE: 17

```
Leu Thr Arg Asp Val Val Asn Ala Pro Asp Ile Ile Asp Ser Arg Glu
1               5                   10                  15

Asn
```

<210> SEQ ID NO 18
<211> LENGTH: 14
<212> TYPE: PRT
<213> ORGANISM: Nicotiana tomentosiformis

<400> SEQUENCE: 18

```
Leu Gly Arg Glu Thr Val Tyr Ala Pro Gly Trp Arg Gln Asn
1               5                   10
```

<210> SEQ ID NO 19
<211> LENGTH: 17
<212> TYPE: PRT
<213> ORGANISM: Solanum lycopersicum

<400> SEQUENCE: 19

Leu Gly Cys Asp Ala Ile Asp Ala Pro Asp Ile Ile Asp Ser Arg Gln
1 5 10 15

Asn

<210> SEQ ID NO 20
<211> LENGTH: 17
<212> TYPE: PRT
<213> ORGANISM: Solanum tuberosum

<400> SEQUENCE: 20

Leu Gly Arg Glu Ala Ile Asn Ala Pro Asp Ile Ile Asp Ser Arg Gln
1 5 10 15

Asn

<210> SEQ ID NO 21
<211> LENGTH: 14
<212> TYPE: PRT
<213> ORGANISM: Beta vulgaris

<400> SEQUENCE: 21

Leu Gly Arg Gln Thr Val Asn Ala Pro Gln Gln Arg Gln Asn
1 5 10

<210> SEQ ID NO 22
<211> LENGTH: 14
<212> TYPE: PRT
<213> ORGANISM: Beta vulgaris

<400> SEQUENCE: 22

Leu Gly Arg Gln Thr Val Tyr Ala Pro Gly Trp Arg Gln Asn
1 5 10

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
atgtcaagac tagatccttt aatag 25

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ttataggtga cggccac 17

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcagcaacag gcgaattgag attatgaaat ctc 33

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
aaacagcggc aacaggcaaa ttgagac 27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
caacatctcg agtcaattgt cgaaacag 28

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
acagtttcgc gacccaattg tc 22

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
aagcaaccca aacctgaggg agtatctg 28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cagatatccc tgcaaccaca gaagcaac 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aattgtccac caacctaggg ttgacgtg 28

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tcacagatat cccagcaact ac 22

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
agatatccct gcaaccacag aagcaac 27

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cattcacaac atctcgagtc aattgtcgaa acag 34

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gatatcccag caactacaga tacaag 26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gaaacgggca aaccaagatt gtaaac 26

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 37

tgagatgcac cacgaagctc                                              20


<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

ccaacattgt caccaggaag tg                                           22


<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

cccctcacca cagagtctgc                                              20


<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

aagggtgttg ttgtcctcaa tctt                                         24


<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

agactcgaga tgtcaagact agatccttta atag                              34


<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

agactcgaga tgttaagagc aaatccttta g                                 31


<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 43

acatctagat tataggtgac ggccac                                            26


<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

agactcgaga tgccaagaat agatcctttg                                        30


<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

acatctagat taatatgcgc ggcggccac                                         29


<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

agactcgaga tgtctataaa tataagagac c                                      31


<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

agatctagac taaagtcttc ttcctccgca g                                      31


<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

agaggtacct cgtaagattt ttagtttgtt c                                      31


<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 49
agactcgagt ttgatggtgt ggaaatgttt ac 32

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
agagtcgact cgtaagattt ttagtttgtt c 31

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
agagtcgacg tcactggatt ttggttttag 30

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
agagtcgaca tgttgtcatc agctaagcat c 31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
agagcggccg cgaaaatgga gctgtggaag 30

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
agagcggccg ctcaaaatgg agctgtggaa g 31

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
agagtcgaca tgtctataaa tataagagac c 31

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
agagcggccg cgaaagtctt cttcctccgc ag 32

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
agagcggccg cctaaagtct tcttcctccg cag 33

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
agagtcgaca tgtcaagact agatcc 26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
agagtcgaca tgttaagagc aaatcc 26

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
agagtcgaca tgccaagaat agatcctttg 30

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
agagcggccg cgataggtga cggccac 27

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
agagcggccg ccgattatag gtgacggcc 29

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
agagcggccg cccatatgcg cggcggccac 30

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
agagcggccg cttaatatgc gcggcggcca c 31

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
agaaccatgg gtaaaggaga ag 22

<210> SEQ ID NO 66
<211> LENGTH: 78
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
agaactcgag tgtttgtata gttcatccat gccatgtgta atcccagcag ctgttactct 60
ctcaagaagg accatgtg 78

<210> SEQ ID NO 67
<211> LENGTH: 9
<212> TYPE: PRT
<213> ORGANISM: Unknown
<220> FEATURE:
<223> OTHER INFORMATION: Description of Unknown: PEBP family peptide motif sequence

<400> SEQUENCE: 67

Val Asn Ala Pro Asp Ile Ile Asp Ser
1               5

<210> SEQ ID NO 68
<211> LENGTH: 9
<212> TYPE: PRT
<213> ORGANISM: Unknown
<220> FEATURE:
<223> OTHER INFORMATION: Description of Unknown:
      PEBP family peptide motif sequence
<220> FEATURE:
<221> NAME/KEY: MOD_RES
<222> LOCATION: (1)..(1)
<223> OTHER INFORMATION: May or may not be present

<400> SEQUENCE: 68

Val Asn Ala Pro Asp Ile Ile Asp Ser
1               5

<210> SEQ ID NO 69
<211> LENGTH: 6
<212> TYPE: PRT
<213> ORGANISM: Unknown
<220> FEATURE:
<223> OTHER INFORMATION: Description of Unknown:
      PEBP family peptide motif sequence
<220> FEATURE:
<221> NAME/KEY: MOD_RES
<222> LOCATION: (1)..(1)
<223> OTHER INFORMATION: May or may not be present

<400> SEQUENCE: 69

Val Tyr Ala Pro Gly Trp
1               5

<210> SEQ ID NO 70
<211> LENGTH: 175
<212> TYPE: PRT
<213> ORGANISM: Arabidopsis thaliana

<400> SEQUENCE: 70

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

```
Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175


<210> SEQ ID NO 71
<211> LENGTH: 177
<212> TYPE: PRT
<213> ORGANISM: Arabidopsis thaliana

<400> SEQUENCE: 71

Met Glu Asn Met Gly Thr Arg Val Ile Glu Pro Leu Ile Met Gly Arg
1               5                   10                  15

Val Val Gly Asp Val Leu Asp Phe Phe Thr Pro Thr Thr Lys Met Asn
            20                  25                  30

Val Ser Tyr Asn Lys Lys Gln Val Ser Asn Gly His Glu Leu Phe Pro
        35                  40                  45

Ser Ser Val Ser Ser Lys Pro Arg Val Glu Ile His Gly Gly Asp Leu
    50                  55                  60

Arg Ser Phe Phe Thr Leu Val Met Ile Asp Pro Asp Val Pro Gly Pro
65                  70                  75                  80

Ser Asp Pro Phe Leu Lys Glu His Leu His Trp Ile Val Thr Asn Ile
                85                  90                  95

Pro Gly Thr Thr Asp Ala Thr Phe Gly Lys Glu Val Val Ser Tyr Glu
            100                 105                 110

Leu Pro Arg Pro Ser Ile Gly Ile His Arg Phe Val Phe Val Leu Phe
        115                 120                 125

Arg Gln Lys Gln Arg Arg Val Ile Phe Pro Asn Ile Pro Ser Arg Asp
    130                 135                 140

His Phe Asn Thr Arg Lys Phe Ala Val Glu Tyr Asp Leu Gly Leu Pro
145                 150                 155                 160

Val Ala Ala Val Phe Phe Asn Ala Gln Arg Glu Thr Ala Ala Arg Lys
                165                 170                 175

Arg


<210> SEQ ID NO 72
<211> LENGTH: 177
<212> TYPE: PRT
<213> ORGANISM: Nicotiana tomentosiformis

<400> SEQUENCE: 72

Met Ser Arg Leu Asp Pro Leu Ile Val Ser Gly Val Ile Gly Asp Val
1               5                   10                  15

Leu Asp Ser Phe Thr Arg Ser Ile Asp Phe Ser Val Val Tyr Asn Asn
            20                  25                  30

Arg Val Gln Val Tyr Asn Gly Cys Gly Leu Arg Pro Ser Gln Ile Val
        35                  40                  45

Asn Gln Pro Arg Val Asp Ile Gly Gly Asp Asp Leu Arg Thr Phe Tyr
    50                  55                  60

Thr Met Val Met Val Asp Pro Asp Ala Pro Thr Pro Ser Asn Pro Asn
65                  70                  75                  80

Leu Arg Glu Tyr Leu His Trp Leu Val Thr Asp Ile Pro Ala Thr Thr
                85                  90                  95

Gly Ala Asn Phe Gly Asn Glu Ile Ile Arg Tyr Glu Ser Pro Arg Pro
            100                 105                 110
```

```
Ser Leu Gly Ile His Arg Tyr Ile Phe Val Leu Phe Gln Gln Leu Asp
        115                 120                 125

Arg Glu Val Val Asn Ala Pro Asp Ile Ile Asp Ser Arg Gln Asn Phe
    130                 135                 140

Asn Thr Arg Asp Phe Ala Arg Phe His Asn Leu Asn Ser Pro Val Ala
145                 150                 155                 160

Ala Val Tyr Phe Asn Cys Asn Arg Glu Gly Gly Thr Gly Gly Arg His
                165                 170                 175

Leu


<210> SEQ ID NO 73
<211> LENGTH: 177
<212> TYPE: PRT
<213> ORGANISM: Nicotiana tomentosiformis

<400> SEQUENCE: 73

Met Leu Arg Ala Asn Pro Leu Val Val Ser Gly Val Ile Gly Asp Val
1               5                   10                  15

Leu Asp Pro Phe Thr Lys Ser Val Asp Phe Asp Val Val Tyr Asn Asn
            20                  25                  30

Asn Val Gln Val Tyr Asn Gly Cys Gly Leu Arg Pro Ser Gln Ile Val
        35                  40                  45

Asn Gln Pro Arg Val Asp Ile Ala Gly Asp Asp Phe Arg Thr Phe Tyr
    50                  55                  60

Thr Leu Val Met Val Asp Pro Asp Ala Pro Thr Pro Ser Asn Pro Asn
65                  70                  75                  80

Leu Arg Glu Tyr Leu His Trp Leu Val Thr Asp Ile Pro Ala Thr Thr
                85                  90                  95

Glu Ala Thr Phe Gly Asn Glu Ile Val Ser Tyr Glu Arg Pro Gln Pro
            100                 105                 110

Ser Leu Gly Ile His Arg Tyr Ile Phe Val Leu Phe Arg Gln Leu Asp
        115                 120                 125

Arg Glu Val Val Asn Ala Pro Asp Ile Ile Asp Ser Arg Glu Ile Phe
    130                 135                 140

Asn Thr Arg Asp Phe Ala Arg Phe His Gly Leu Asn Leu Pro Val Ala
145                 150                 155                 160

Ala Val Tyr Phe Asn Cys Asn Arg Glu Gly Gly Thr Gly Gly Arg His
                165                 170                 175

Leu


<210> SEQ ID NO 74
<211> LENGTH: 177
<212> TYPE: PRT
<213> ORGANISM: Nicotiana tomentosiformis

<400> SEQUENCE: 74

Met Ser Arg Leu Asp Pro Leu Ile Val Ser Gly Val Ile Gly Asp Val
1               5                   10                  15

Leu Asp Pro Phe Thr Arg Ser Ile Asp Phe Asn Val Val Tyr Asn Asn
            20                  25                  30

Arg Met Gln Val Tyr Asn Gly Cys Gly Leu Arg Pro Ser Gln Ile Val
        35                  40                  45

His Gln Pro Arg Val Asp Val Gly Gly Asp Asp Leu Arg Thr Phe Tyr
    50                  55                  60

Thr Leu Val Met Val Asp Pro Asp Ala Pro Thr Pro Ser Asn Pro Asn
65                  70                  75                  80
```

```
Gln Arg Glu Tyr Leu His Trp Leu Val Thr Asn Ile Pro Ala Thr Thr
                85                  90                  95

Gly Ala His Phe Gly Asn Glu Ile Ile Gln Tyr Glu Ser Pro Arg Pro
            100                 105                 110

Ser Leu Gly Ile His Arg Tyr Ile Phe Val Leu Phe Arg Gln Leu Thr
        115                 120                 125

Arg Asp Val Val Asn Ala Pro Asp Ile Ile Asp Ser Arg Glu Asn Phe
    130                 135                 140

Asn Thr Arg Asp Phe Ala Arg Phe Tyr Asp Leu Asn Ser Pro Val Ala
145                 150                 155                 160

Ala Met Tyr Phe Asn Ser Asn Arg Glu Ser Gly Thr Gly Gly Arg His
                165                 170                 175

Leu


<210> SEQ ID NO 75
<211> LENGTH: 174
<212> TYPE: PRT
<213> ORGANISM: Nicotiana tomentosiformis

<400> SEQUENCE: 75

Met Pro Arg Ile Asp Pro Leu Ile Val Gly Gly Val Val Gly Asp Val
1               5                   10                  15

Leu Asp Leu Phe Thr Arg Ser Val Asp Leu Arg Val Val Tyr Asn Asn
            20                  25                  30

Lys Glu Val Asn Asn Ala Cys Gly Leu Lys Pro Ser Gln Ile Val Thr
        35                  40                  45

Gln Pro Arg Val Gln Ile Gly Gly Asp Asp Leu Arg Asn Phe Tyr Thr
    50                  55                  60

Leu Val Met Val Asp Pro Asp Ala Pro Ser Pro Ser Asn Pro Asn Leu
65                  70                  75                  80

Arg Glu Tyr Leu His Trp Leu Val Thr Asp Ile Pro Ala Thr Thr Asp
                85                  90                  95

Thr Ser Phe Gly Asn Glu Val Val Cys Tyr Glu Ser Pro Gln Pro Ser
            100                 105                 110

Met Gly Ile His Arg Phe Val Phe Ala Leu Phe Arg Gln Leu Gly Arg
        115                 120                 125

Glu Thr Val Tyr Ala Pro Gly Trp Arg Gln Asn Phe Asn Thr Arg Asp
    130                 135                 140

Phe Ala Glu Leu Tyr Asn Leu Gly Leu Pro Val Ala Ala Val Tyr Phe
145                 150                 155                 160

Asn Cys His Arg Glu Ser Gly Thr Gly Gly Arg Arg Ala Tyr
                165                 170


<210> SEQ ID NO 76
<211> LENGTH: 174
<212> TYPE: PRT
<213> ORGANISM: Nicotiana tabacum

<400> SEQUENCE: 76

Met Ala Ser Arg Val Val Glu Pro Leu Val Val Ala Arg Val Ile Gly
1               5                   10                  15

Glu Val Val Asp Ser Phe Asn Pro Ser Val Lys Leu Asn Val Ile Tyr
            20                  25                  30

Asn Gly Ser Lys Gln Val Phe Asn Gly His Glu Leu Met Pro Ala Val
        35                  40                  45
```

```
Ile Ala Ala Lys Pro Arg Val Glu Ile Gly Gly Glu Asp Met Arg Ser
    50                  55                  60

Ala Tyr Thr Leu Ile Met Thr Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Ser Thr Asp Ser Ser Phe Gly Arg Glu Ile Val Ser Tyr Glu Ser Pro
            100                 105                 110

Lys Pro Val Ile Gly Ile His Arg Tyr Val Leu Leu Leu Tyr Lys Gln
        115                 120                 125

Ser Gly Arg Gln Thr Val Lys Pro Ala Ala Thr Arg Asp His Phe Asn
    130                 135                 140

Thr Arg Arg Tyr Thr Ala Glu Asn Gly Leu Gly Ser Pro Val Ala Ala
145                 150                 155                 160

Val Tyr Phe Asn Ala Gln Arg Glu Thr Ala Ala Arg Arg Arg
                165                 170


<210> SEQ ID NO 77
<211> LENGTH: 175
<212> TYPE: PRT
<213> ORGANISM: Nicotiana tabacum

<400> SEQUENCE: 77

Met Gly Ser Lys Met Ser Asp Pro Leu Val Ile Gly Arg Val Ile Gly
1               5                   10                  15

Glu Val Val Asp Tyr Phe Thr Pro Ser Val Lys Met Ser Val Thr Tyr
            20                  25                  30

Asn Ser Ser Lys His Val Tyr Asn Gly His Glu Leu Phe Pro Ser Ser
        35                  40                  45

Val Thr Ser Lys Pro Arg Val Glu Val His Gly Gly Asp Leu Arg Ser
    50                  55                  60

Phe Phe Thr Met Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Lys Glu Ile Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Val Leu Thr Ala Pro Leu Ser Arg Asp Arg Phe
    130                 135                 140

Asn Thr Arg Lys Phe Ala Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175


<210> SEQ ID NO 78
<211> LENGTH: 175
<212> TYPE: PRT
<213> ORGANISM: Nicotiana tabacum

<400> SEQUENCE: 78

Met Gly Ser Lys Met Ser Asp Pro Leu Val Ile Gly Arg Val Ile Gly
1               5                   10                  15

Glu Val Val Asp Tyr Phe Thr Pro Ser Val Lys Met Ser Val Thr Tyr
            20                  25                  30
```

```
Asn Ser Ser Lys His Val Tyr Asn Gly His Glu Leu Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Ile Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Leu Leu Ser Ala Pro Leu Ser Arg Asp Arg Phe
    130                 135                 140

Asn Thr Arg Lys Phe Ser Glu Glu Asn Glu Leu Gly Ser Pro Val Ala
145                 150                 155                 160

Ala Ala Phe Phe Asn Cys Gln Arg Glu Thr Ala Ala Arg Arg Arg
                165                 170                 175


<210> SEQ ID NO 79
<211> LENGTH: 175
<212> TYPE: PRT
<213> ORGANISM: Solanum tuberosum

<400> SEQUENCE: 79

Met Pro Arg Asp Pro Leu Ile Val Ser Gly Val Val Gly Asp Val Val
1               5                   10                  15

Asp Pro Phe Thr Arg Cys Val Asp Phe Gly Val Val Tyr Asn Asn Arg
            20                  25                  30

Val Val Tyr Asn Gly Cys Ala Leu Arg Pro Ser Gln Val Val Asn Gln
        35                  40                  45

Pro Arg Val Asp Ile Gly Gly Asp Asp Leu Arg Ile Phe Tyr Thr Leu
    50                  55                  60

Ile Met Val Asp Pro Asp Ala Pro Asn Pro Ser Asn Pro Asn Leu Arg
65                  70                  75                  80

Glu Tyr Leu His Trp Leu Val Thr Asp Ile Pro Ala Thr Thr Gly Ala
                85                  90                  95

Thr Phe Gly Asn Glu Val Val His Tyr Glu Ser Pro Arg Pro Ser Met
            100                 105                 110

Gly Ile His Arg Tyr Ile Phe Val Leu Phe Gln Gln Leu Gly Arg Glu
        115                 120                 125

Ala Ile Asn Ala Pro Asp Ile Ile Asp Ser Arg Gln Asn Phe Asn Thr
    130                 135                 140

Arg Asp Phe Ala Arg Phe His Asn Leu Gly Leu Pro Val Ala Ala Val
145                 150                 155                 160

Tyr Phe Asn Cys Asn Arg Glu Gly Gly Thr Gly Asp Arg Arg Leu
                165                 170                 175


<210> SEQ ID NO 80
<211> LENGTH: 175
<212> TYPE: PRT
<213> ORGANISM: Solanum lycopersicum
```

<400> SEQUENCE: 80

Met Pro Arg Asp Pro Leu Ile Val Ser Gly Val Val Gly Asp Val Val
1 5 10 15

Asp Pro Phe Thr Arg Cys Val Asp Phe Gly Val Val Tyr Asn Asn Arg
20 25 30

Val Val Tyr Asn Gly Cys Ser Leu Arg Pro Ser Gln Val Asn Asn Gln
35 40 45

Pro Arg Val Asp Ile Asp Gly Asp Asp Leu Arg Thr Phe Tyr Thr Leu
50 55 60

Ile Met Val Asp Pro Asp Ala Pro Asn Pro Ser Asn Pro Asn Leu Arg
65 70 75 80

Glu Tyr Leu His Trp Leu Val Thr Asp Ile Pro Ala Ala Thr Gly Ala
85 90 95

Thr Phe Gly Asn Glu Val Val Gly Tyr Glu Ser Pro Arg Pro Ser Met
100 105 110

Gly Ile His Arg Tyr Ile Phe Val Leu Tyr Arg Gln Leu Gly Cys Asp
115 120 125

Ala Ile Asp Ala Pro Asp Ile Ile Asp Ser Arg Gln Asn Phe Asn Thr
130 135 140

Arg Asp Phe Ala Arg Phe His Asn Leu Gly Leu Pro Val Ala Ala Val
145 150 155 160

Tyr Phe Asn Cys Asn Arg Glu Gly Gly Thr Gly Gly Arg Arg Leu
165 170 175

<210> SEQ ID NO 81
<211> LENGTH: 179
<212> TYPE: PRT
<213> ORGANISM: Beta vulgaris

<400> SEQUENCE: 81

Met Pro Arg Thr Ser Ala Ser Ala Pro Arg Asp Pro Leu Val Leu Gly
1 5 10 15

Gly Val Ile Gly Asp Val Leu Glu Pro Phe Glu Arg Ser Val Thr Leu
20 25 30

Lys Ile Ser Phe Asn Asn Arg Asn Val Asn Asn Gly Gly Asp Phe Arg
35 40 45

Pro Ser Gln Val Val Asn Gln Pro Arg Val Glu Val Gly Gly Asp Asp
50 55 60

Leu Arg Thr Cys Tyr Thr Leu Val Met Val Asp Pro Asp Ala Pro Ser
65 70 75 80

Pro Ser Asn Pro His Gln Arg Glu Tyr Leu His Trp Leu Val Thr Asp
85 90 95

Ile Pro Gly Thr Thr Ser Ala Ser Phe Gly Glu Glu Ile Val Tyr Tyr
100 105 110

Glu Asn Pro Arg Pro Ser Thr Gly Ile His Arg Phe Val Phe Ala Leu
115 120 125

Phe Arg Gln Leu Gly Arg Gln Thr Val Asn Ala Pro Gln Gln Arg Gln
130 135 140

Asn Phe Asn Thr Arg Asp Phe Ala Glu Leu Tyr Asn Leu Gly Leu Pro
145 150 155 160

Val Ala Ala Val Tyr Phe Asn Cys Gln Arg Glu Gly Gly Cys Gly Gly
165 170 175

Arg Arg Phe

-continued

```
<210> SEQ ID NO 82
<211> LENGTH: 175
<212> TYPE: PRT
<213> ORGANISM: Beta vulgaris

<400> SEQUENCE: 82

Met Pro Arg Ala Pro Arg Asp Pro Leu Val Val Gly Arg Val Ile Gly
1               5                   10                  15

Asp Val Leu Asp Pro Phe Ser Arg Thr Val Asn Leu Arg Val Ser Tyr
            20                  25                  30

Ser Asn Arg Asp Val Asn Asn Gly Cys Glu Leu Arg Pro Ser Gln Val
        35                  40                  45

Val Asn Gln Pro Arg Val Glu Val Gly Gly Asp Asp Leu Arg Thr Phe
    50                  55                  60

Tyr Thr Leu Val Met Val Asp Pro Asp Ala Pro Ser Pro Ser Asn Pro
65                  70                  75                  80

His Leu Arg Glu Tyr Leu His Trp Leu Val Thr Asp Ile Pro Gly Thr
                85                  90                  95

Thr Gly Ala Ser Phe Gly Gln Glu Val Val Cys Tyr Glu Asn Pro Arg
            100                 105                 110

Pro Ser Val Gly Ile His Arg Phe Ile Leu Val Leu Phe Arg Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Leu Pro Val Ala Ala Val
145                 150                 155                 160

Tyr Phe Asn Cys Gln Arg Glu Gly Gly Ser Gly Gly Arg Arg Leu
                165                 170                 175


<210> SEQ ID NO 83
<211> LENGTH: 14
<212> TYPE: PRT
<213> ORGANISM: Nicotiana tomentosiformis

<400> SEQUENCE: 83

Leu Asp Arg Glu Val Val Tyr Ala Pro Gly Trp Arg Gln Asn
1               5                   10
```

What is claimed is:

1. A transgenic plant, part of a transgenic plant, or seed of a transgenic plant, in which the development of flowering is suppressed, repressed or delayed, wherein the plant, part or seed comprises a nucleic acid sequence, which consists of any of the sequences of SEQ ID NO: 1, 2 or 3, wherein said nucleic acid is heterologous with respect to the plant, its part or its seed, wherein said nucleic acid sequence codes for a protein that phylogenetically belongs to the FT-clade of the PEBP gene family, and wherein the protein consists of any of the sequences of SEQ ID NO: 5, 6 or 7.

2. A transgenic plant, part of a transgenic plant, or seed of a transgenic plant according to claim 1, wherein the nucleic acid sequence further comprises a component which is able to function as a promoter.

3. A transgenic plant, part of a transgenic plant, or seed of a transgenic plant according to claim 2, wherein the promoter is selected from the group consisting of cell specific promoters, temporally inducible promoters, promoters originally present in tobacco plants, tobacco-derived tissue specific promoters, tobacco-derived cell specific promoters, over the course of time constitutive active promoters, promoters derived from another plant, tissue specific constitutive active promoters, cell specific constitutive active promoters, over the course of time constitutive active promoters, synthetic promoters, and promoters having a combination of functions enumerated above.

4. A transgenic plant, part of a transgenic plant, or seed of a transgenic plant according to claim 2, wherein the nucleic acid sequence, which is able to function as a promoter, will upregulate expression of the nucleic acid.

5. A transgenic plant according to claim 1, comprising a vector and wherein the development of flowering of the transgenic plant is suppressed, repressed or delayed.

6. A transgenic plant according to claim 5, wherein the vector is a binary vector.

7. A transgenic plant according to claim 6, wherein the binary vector carries an antibiotic, a metabolic or a herbicide resistance gene that is under the control of a temporal and spatial constitutive active promoter or of a temporally inducible promoter.

8. A transgenic plant according to claim 7, wherein the antibiotic resistance gene is selected from the group consisting of the kanamycin gene and the hygromycin gene, wherein the herbicide resistance gene is the BASTA resistance gene and wherein the antibiotic, metabolic or herbicide resistance gene is under the control of the nos, the 35SCaMV promoter or the ethanol inducible 35SCaMV promoter.

9. A transgenic plant, part of a transgenic plant or seed of a transgenic plant as claimed in claim 1, which is a member of the Solanaceae plant family.

10. A transgenic plant, part of a transgenic plant or seed of a transgenic plant as claimed in claim 1, which is a member of the Brassicaceae plant family.

11. A transgenic plant, part of a transgenic plant, or seed of a transgenic plant according to claim 1, wherein the nucleic acid is under the control of a constitutive promoter.

12. A DNA molecule, which codes for a protein consisting of any one of the sequences as indicated in SEQ ID No. 5, 6, and 7, or wherein the DNA molecule consists of any one of the sequences of SEQ ID No. 1, 2, 3.

13. The DNA molecule according to claim 12, wherein the nucleic acid is operably linked to a promoter, wherein the promoter is selected under cell specific promoters, temporally inducible promoters, promoters originally present in tobacco plants, tobacco-derived tissue specific and/or cell specific promoters, over the course of time constitutive active promoters, tissue specific and/or cell specific and/or over the course of time constitutive active promoters, commercially available promoters, synthetic promoters, or under promoters having a combination of functions enumerated above.

14. A vector, comprising the DNA molecule of claim 12.

15. The vector according to claim 14, wherein the vector is a binary vector comprising an antibiotic, a metabolic or a herbicide resistance gene.

* * * * *